(12) United States Patent
Yan

(10) Patent No.: US 10,119,896 B2
(45) Date of Patent: Nov. 6, 2018

(54) ELECTROMECHANICAL TRANSDUCERS FOR FLUID VISCOSITY MEASUREMENT

(71) Applicant: Xiang Yan, Waltham, MA (US)

(72) Inventor: Xiang Yan, Waltham, MA (US)

( * ) Notice: Subject to any disclaimer, the term of this patent is extended or adjusted under 35 U.S.C. 154(b) by 66 days.

(21) Appl. No.: 15/384,568

(22) Filed: Dec. 20, 2016

(65) Prior Publication Data

US 2017/0191918 A1    Jul. 6, 2017

Related U.S. Application Data

(60) Provisional application No. 62/273,785, filed on Dec. 31, 2015.

(51) Int. Cl.
| | | |
|---|---|---|
| *G01N 11/16* | (2006.01) | |
| *B06B 1/06* | (2006.01) | |
| *G01H 13/00* | (2006.01) | |

(52) U.S. Cl.
CPC .......... *G01N 11/16* (2013.01); *B06B 1/0603* (2013.01); *G01H 13/00* (2013.01)

(58) Field of Classification Search
CPC ..................................................... G01N 11/16
See application file for complete search history.

(56) References Cited

U.S. PATENT DOCUMENTS

| | | | | |
|---|---|---|---|---|
| 2,696,735 A | * | 12/1954 | Woodward | G01N 11/16 73/54.26 |
| 4,488,427 A | * | 12/1984 | Matusik | G01N 11/162 73/54.23 |
| 4,602,505 A | | 7/1986 | Suzuki | |
| 4,729,237 A | | 3/1988 | Suzuki | |
| 4,941,346 A | * | 7/1990 | Suzuki | G01N 11/16 73/54.41 |
| 5,067,344 A | * | 11/1991 | Fitzgerald | G01N 11/16 73/32 A |
| 6,044,694 A | | 4/2000 | Anderson | |
| 6,250,136 B1 | * | 6/2001 | Igreja | G01F 23/2965 73/54.24 |
| 2005/0069864 A1 | * | 3/2005 | Itoh | G01N 5/00 435/4 |
| 2018/0074018 A1 | * | 3/2018 | Kuhnen | G01F 23/2968 |

OTHER PUBLICATIONS

A&D Company, Limited, SV-A Series, Sine-wave Vibro Viscometer Users' Handbook (Year: 2009).*
J,G,Woodward. A vibrating-plate Viscometer, Journal of colloid Science, 01, 1953.
W,Y,Shih; X,Li; H,Gu;W-H Shih; I,A,Aksay; Simultaneous liquid viscosity and density determination with piezoelectric uniform cantilevers. Journal of Applied Physcis, vol. 89, No. 2, 2001, p. 1497-1505.

* cited by examiner

Primary Examiner — Charlie Y Peng

(57) ABSTRACT

Electromechanical transducers and methods are disclosed for measuring fluid parameters, including viscosity and product of viscosity and density. The said transducers utilize the electromechanical transduction materials to excite and measure the vibration of composite beam(s) with sensor plate(s) attached to the end(s) of the beam(s). The fluid viscous force acted on the surfaces of the sensor plate(s) damps the beams' vibration. The voltage output or the change of the electrical conductance of the transducer can be used to measure fluid parameters.

11 Claims, 18 Drawing Sheets

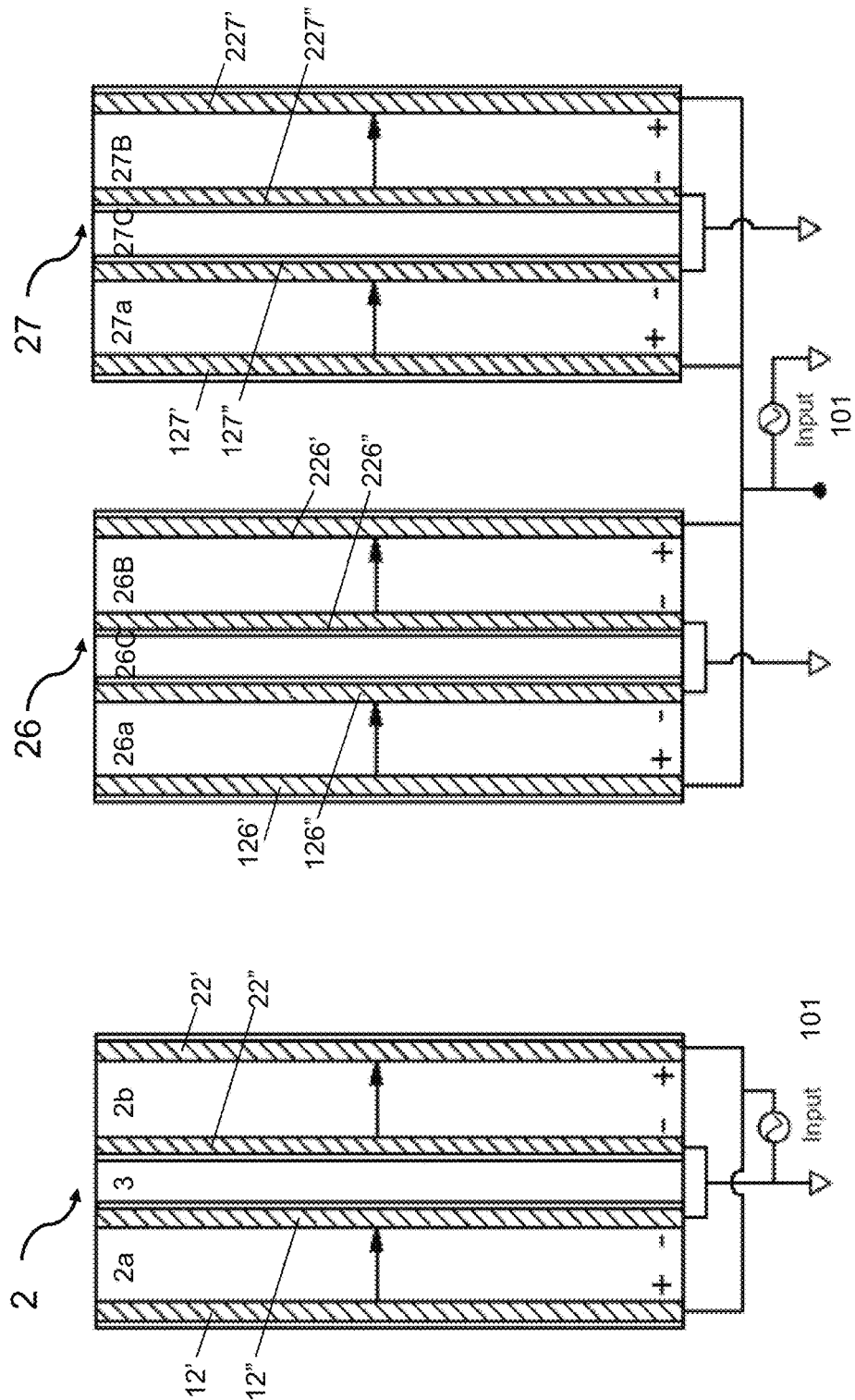

ELECTROMECHANICAL TRANSDUCERS FOR FLUID VISCOSITY MEASUREMENT

RELATED APPLICATION(S)

Provisional application No. 62/273,785 filed on Dec. 31, 2015.

BACKGROUND OF THE INVENTION

Field of the Invention

The present invention relates to fluid property measuring transducers and methods and, more particularly, to electromechanical transducers and associated methods that can determine the viscosity of a fluid.

Description of the Related Art

Viscosity is one of the most sensitive and essential characteristics that determines a fluid's quality. It is important in many industrial and scientific applications. The transducers used for measuring viscosity are classified based on how the flow is initiated or maintained. Common types include: Rotational, Falling object, Capillary, Vibration and Ultrasonic, with the later two induce oscillatory motions in the fluid. Vibrational transducer has certain advantages that are used widely as process viscometers. Vibrational transducers are operated by measuring the damping of an oscillating resonator immersed in a testing fluid. The resonator is excited into either torsional or linear oscillation via means of electromeganetic induction or piezoelectric effect. Resonators that employ linear vibrating beams are described by J. G. Woodward in "A Vibrating Plate Viscometer", Journal of Colloid Science, 1953 followed by his own U.S. Pat. No. 2,696,735 and also by U.S. Pat. No. 5,067,344 where a vibrating bar with a tip blade is used to generate shear oscillation of the fluid. A tuning fork transducer described in U.S. Pat. No. 4,729,237 employs a pair of vibrating beams with integrated sensor plates as resonators. The vibrating beams are driven in anti-phase as in a tuning fork and a separate detector is used to measure the amplitudes. In the described arts, the driver and pick up transducers are separated from the resonators which require additional means of support and operate the transducers.

U.S. Pat. No. 6,044,694 describes an integrated piezoelectric bender type transducer for measuring viscosity and density of the fluid, which has the merit of small footprint, simple construction and low cost. However the vibration of the bender not only excites shear wave but also appreciable amount of compression wave in the fluid. The resonant frequency change and the damping of the transducer are influenced by both the density and viscosity of the fluid. The detailed analysis is described by W. Y. Shih et. al in "Simultaneous liquid viscosity and density determination with piezoelectric uniform cantilevers", Journal of Applied Physics, 2001. In the described art, the determination of viscosity and density from damping and resonant frequency separately is based on an oscillating sphere model and is applicable to a limited range of viscosities.

A novel type of vibrational electromechanical transducer and the measurement principle are disclosed in the current invention that will address some of the aforementioned problems. The transducer comprises of composite beam and sensor plate, while the composite beam has integrated electromechanical transduction materials for driving and sensing the transducer response. The sensor plate is attached at the amplitude anti-node of the composite beam for optimization of the transducer's response to fluid viscosity. The sensor plate is orthogonal to the composite beams such that when the composite beam is excited into bending vibration, the motion of the sensor plate is along its plane. A pure shear oscillation of the fluid can be excited around the sensor plate. Although density influence on damping of the transducer is not completely eliminated, it can be accurately predicted. The transducer's resonant frequency, amplitude or electrical conductance can be measured to obtain a response function. The response function has proved relation to the viscosity and density of the fluid. The current invention also provides several means of excitation and sensing that optimize the response of the transducer to fluid viscosity. The advantages of the current transducer owns to its simple, robust, cost-effective construction, ease of measurement and yet with improved accuracy.

SUMMARY OF THE INVENTION

The subject invention relates to electromechanical transducers for measuring viscosity of the fluids. In one embodiment the electromechanical transducer comprises a composite beam, at least one sensor plate attached to one end of the composite beam, and a support structure fixed to the other end of the composite beam. The composite beam comprises of a substrate with two electromechanical transduction materials bonded to its major surfaces. The normal direction of the sensor plate is orthogonal to the normal direction of the major surfaces of the composite beam.

In another embodiment, the electromechanical transducer comprises multiple composite beams of equal lengths, at least one sensor plate, one connector and one support structure. The composite beams are fixed to the support structure at one common end. The connector mechanically joins all the composite beams at the other end with at least one sensor plate attached to it. Each said composite beam comprises of a substrate with at least one electromechanical transduction material bonded to its major surfaces. The normal direction of the sensor plate is orthogonal to the normal direction of the major surfaces of the composite beams.

In the described embodiments, the electromechanical transduction materials of the said composite beams are any suitable piezoelectric materials. Alternatively they can be any suitable magnetostrictive or electrostrictive materials. At least one said composite beam may comprise of thin rectangular piezoelectric plates having electrodes applied on the major surfaces and may be polarized along the thickness directions. Alternatively, the thin rectangular piezoelectric plates may have narrow stripped electrodes on the major surfaces and be tangentially polarized along the length direction of the plates. Alternatively, the thin rectangular piezoelectric plates maybe assembled by bonding multiple piezoelectric segments at their electrode surfaces. The piezoelectric plates maybe polarized along the length directions through the said segments.

According to one aspect of the invention, an electric input voltage may be supplied to at least one piezoelectric plate of the said transducer to excite vibrations of the composite beams and the sensor plate. The sensor plate is immersed in the fluid. The vibration of which excites shear oscillation of the fluid surround the sensor plate. The vibrations of the composite beams are damped due to the fluid's viscous force acted on the surfaces of the sensor plate. The changes in resonant frequency and amplitude may be measured by at least one separate piezoelectric plate of the said transducer. The results of which can be used to determine the viscosity of the fluid. This method is noted as voltage response method.

According to another aspect of the invention, an electrical input voltage may be supplied to all the piezoelectric plates of the said transducer to excite vibrations of the composite beams and the sensor plate. The sensor plate is immersed in the fluid. The vibration of which excites shear oscillations of the fluid surround the sensor plate. The mechanical load of the composite beams, in terms of masses and losses, are increased due to viscous force of the fluid acted on the surfaces of the sensor plate. As a result, the resonant frequency and input electrical conductance of the said transducer are decreased. The resonant frequency and electrical conductance can be obtained through measurement of the electrical impedance of the said transducer, methods of which are well known to those skilled in the art. The measured resonant frequency and electrical conductance can be used to determine the viscosity of the fluid. This method is noted as conductance response method.

In one embodiment of the subject invention, the said transducer comprises one composite beam with a thin metal substrate sandwiched between two piezoelectric plates. At one end, the composite beam is soldered or brazed onto a supporting structure. The supporting structure has significantly larger stiffness and mass than that of the composite beam such that the composite beam can be considered fixed at this end during vibration. At least one sensor plate, for example a thin circular disk and free of any sharp edges, is attached to the other end of the composite beam. The mass and size of the sensor disk is preferably smaller than the mass and size of the composite beam. The normal direction of the disk surface is orthogonal to the normal direction of the major surfaces of the composite beam. An alternating electric voltage with the capability of frequency sweeping is supplied to one piezoelectric plate, termed as actuator. When the frequency of the supplied voltage coincides with the first bending resonant frequency of the composite beam, the said beam is excited into resonant oscillation with amplitude anti-node at the sensor disk end. The sensor disk oscillates along its plane shearing the fluid surround it. The oscillation of the fluid decreases exponentially away from the surfaces of the sensor disk. The motion of the fluid and resulting viscous force have effects of adding mechanical mass and loss to the composite beam and effectively decrease its resonant frequency and the vibration amplitude. These additional mechanical mass and loss are proportional to the surface area of the sensor disk and the square root of the product of the density and viscosity of the fluid. Due to vibration of the composite beam, a voltage is generated at the electrode surfaces of the second piezoelectric plate, therefore termed as receiver.

In another embodiment of the subject invention, the electromechanical transducer comprises at least two parallel composite beams with identical lengths, each of which comprises of a thin metal substrate with at least one piezoelectric plate bonded onto its major surface. At one end, the composite beams are soldered or brazed to a common supporting structure. The supporting structure has mass and stiffness significantly larger than that of the composite beams, such that all the composite beams can be considered fixed at this end during vibration. At the other end of the composite beams, a stiff light connector mechanically joins all the composite beams such that at this end all the beams vibrate in phase relative to each other. At least one sensor plate, for example a thin circular disk and free of any sharp edges, maybe attached to this end and vibrates in phase with all the composite beams. The mass and size of the sensor disk is preferably smaller than the mass and size of the composite beams. The normal direction of the disk surface is perpendicular to the normal direction of the major surfaces of the composite beams. An alternating electric voltage with the capability of frequency sweeping is supplied to at least two piezoelectric plates, termed as actuators. The said actuators have the same polarizations and are electrically connected in parallel. This electrical configuration for the actuator has the merit of increasing vibration amplitude of the composite beams per same input voltage. The rest of the piezoelectric plates are grouped in pairs with opposite polarizations with respect to each other. The two piezoelectric plates in each pair are electrically connected in series. The pairs are then electrically connected in series. This electrical configuration for the receiver has the merit of increasing the output voltage per same vibration amplitude of the composite beams.

According to the previous embodiments, when supplying a sinusoidal input voltage to the actuator(s), the generated open circuit output voltage from the receiver(s) is also sinusoidal with the same frequency as the input signal. When the said transducer vibrates at resonant frequencies, the open circuit output voltage has 90° phase shift with respect to the input voltage. A frequency response function can be defined based on the resonant frequencies and corresponding open circuit output voltages when the transducer vibrates in air and in the fluid respectively. The frequency response function is directly related to the square root of the product of the density and viscosity of the fluid and can he used to determine the viscosity of the fluid.

In yet another embodiment of the subject invention, the electromechanical transducer comprises at least one composite beam. At one end, the composite beam is soldered or brazed onto a supporting structure. The supporting structure has significantly larger stiffness and mass than that of the composite beam such that the composite beam can be considered fixed at this end during vibration. At least one sensor plate, for example a thin circular disk and free of any sharp edges, is attached to the other end of the composite beam. The mass and size of the sensor disk is preferably smaller than the mass and size of the composite beam. The normal direction of the disk surface is perpendicular to the normal direction of the major surfaces of the composite beam. Each said composite beam has at least one piezoelectric plate bonded to its major surface. All the piezoelectric plates are polarized in the same directions and are electrically connected in parallel to be used as actuator. This electrical configuration has the merit of increasing vibration amplitude of the composite beam per the same input voltage. An alternating electric voltage with the capability of frequency sweeping is supplied to the actuator. When the frequency of the supplied voltage coincides with the first bending resonant frequency of the composite beam, the composite beam is excited into resonant oscillation with amplitude anti-node at the sensor disk end. The sensor disk oscillates along its plane shearing the fluid surround it. The oscillation of the fluid decreases exponentially away from the surfaces of the sensor disk. The motion of the fluid and resulting viscous force have effects of adding mechanical mass and loss to the composite beam and effectively decreases the resonant frequency and electrical conductance of the electromechanical transducer.

According to the previous embodiment, the said transducer has resonant frequency determined as the frequency where conductance reaches its maximum value. An conductance response can be defined based on the conductance at the resonant frequency when the transducer operates in air and in the fluid respectively. This conductance response is proportional to the square root of the product of the density and viscosity of the fluid and can be used to determine the viscosity of the fluid.

According to one aspect of the present invention, the said transducer may also have means for its electrical connections attached to a suitable enclosure at the support structure end. The enclosure contains necessary electronics for processing signals to determine viscosity of the fluid. There may also have means of mechanical isolation between support structure and the enclosure to minimize influences from external vibrations.

It is therefore an object of the present invention to provide electromechanical transducers and the associate methods for measuring fluid viscosity. The said transducers are capable of improving measurement range and sensitivity by properly sizing the sensor plate, the amount of piezoelectric materials utilized and the electrical configurations for the actuator and receiver.

It is another object of the present invention to provide means of excitation of fluid into shear oscillations by driving composite beam(s) into bending vibration with the sensor plate(s) attached to the amplitude anti-node. Having the sensor plate(s) oriented orthogonal to the major surfaces of the composite beam(s), the vibration of sensor plate(s) is parallel to its surfaces. The fluid surround the sensor disk(s) is excited into shear oscillation having the same frequency as the composite beam(s). The viscous force and the damping of the said transducer can be accurately predicted.

It is yet another object of the present invention to provide robust, power efficient and cost-effective electromechanical transducers with the sensing element, driving and receiving elements to be able to integrate onto one mechanical assembly.

It is yet another object of the present invention to provide fluid shear rate at definable frequency and definable amplitude which can be controlled by the resonance and amplitude of the composite beams. The induced shear deformation of the fluid is concentrated to the surface of the sensor plate within one viscous penetration length of the fluid and decay exponentially with distance. Thus, agitation or turbulence outside the viscous penetration length will not affect the measurement.

It is yet another object of the present invention to provide electromechanical transducers and the associate methods to simplify the measurement system. From the perspective of the electronic design, it is desirable to characterize the transducer behavior in terms of frequency response and electrical impedance. Such methods can be utilized to determine the viscosity of the fluid. Multiple mechanical assemblies and sensors employed in the prior arts in order to excite and measure the transducer response can be simplified.

There has thus been outlined, rather broadly, the more important features of electromechanical transducers and methods in order that the detailed description thereof that follows may be better understood, and in order that the present contribution to the art may be better appreciated. To the accomplishment of the foregoing and related ends, certain illustrative aspects are described, herein in connection with the following description and the annexed drawings. These aspects are indicative of the various ways in which the principles disclosed herein may be practice and all aspects and equivalents thereof are intended to be within the scope of the claimed subject matter. Other advantages and novel features will become apparent from the following detailed description when considered in conjunction with the drawings.

In this respect, before explaining at least one embodiment of the system in detail, it is to be understood that the electromechanical transducers and methods are not limited in their applications to the details of constructions and to the arrangements of the components set forth in the following descriptions or illustrated in the drawings. The systems are capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

FIGS. 14A, 14B, 14C and 14D illustrate various embodiments of the electric configurations for the electromechanical transducer using conductance response method.

DETAILED DESCRIPTION OF EMBODIMENTS OF THE INVENTION

The present invention now will be described more fully hereinafter with reference to the accompanying drawings and mathematics to fully convey the scope of the invention to those skilled in the art.

Figure 1:
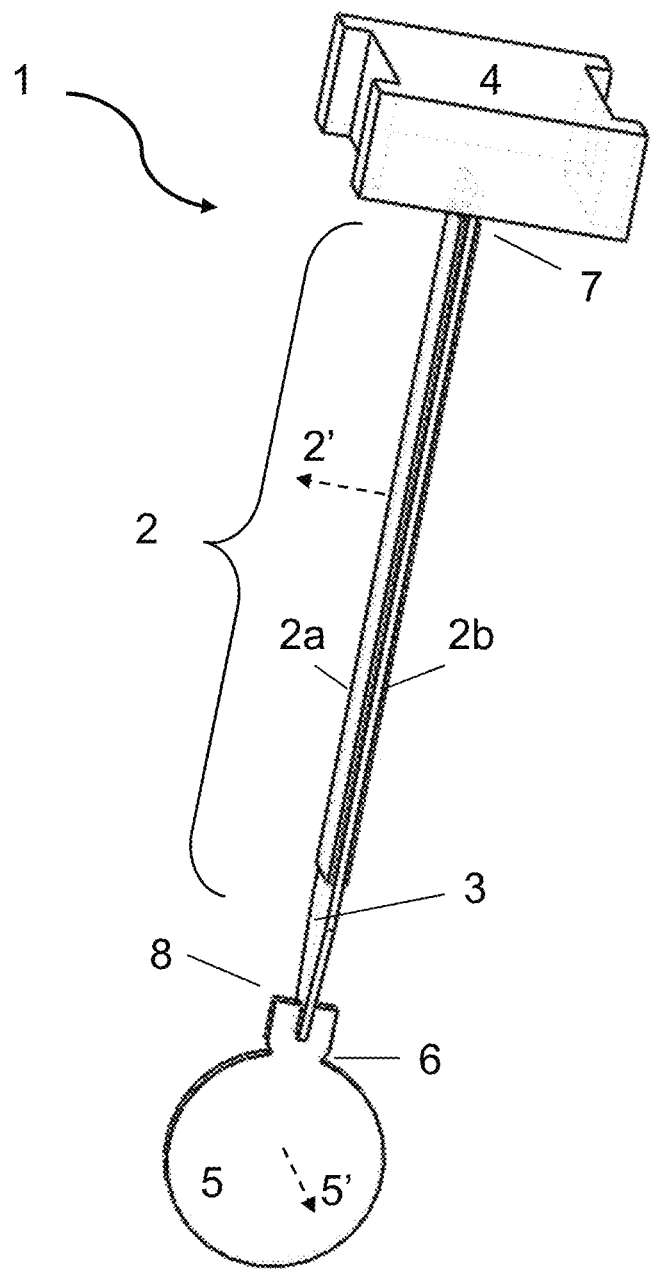
FIG. 1 illustrates a perspective view of one embodiment of the electromechanical transducer.

FIG. 1 illustrates a perspective view of one embodiment of the electromechanical transducer 1. In one embodiment, the transducer 1 comprises one composite beam 2, wherein the composite beam 2 has a proximal end 7 and a distal end 8. The said composite beam comprises of a thin metal substrate 3. Two piezoelectric materials 2a and 2b are bonded to the substrate 3 through proper adhesives. The width of the composite beam 2 is appreciably larger than its thickness. At proximal end 7, the composite beam 2 is brazed or welded onto a supporting structure 4. The supporting structure 4 has significantly larger stiffness and mass than that of the composite beam 2. At least one sensor plate 5, with surface dimension significantly larger than its thickness, is fixed to the distal end 8 of the composite beam 2. The mass and size of the sensor plate 5 is appreciably smaller than the mass and size of the composite beam 2. The normal direction of the plate surface 5' is orthogonal to the normal direction of the surface of the composite beam 2'. The sensor plate 5 may have a recess 6 near the distal end 8. When said sensor plate is immersed into the testing fluid the recess 6 flushes with the surface of the fluid. The sensor plate 5 may be made from the same material as the metal substrate 3. Alternatively, the sensor plate 5 may be made from a specialty alloy that is chemically inert to the testing fluid. The said sensor plate may be brazed or welded onto the metal substrate 3. The center of gravity of the sensor plate 5 and the center of gravity of the composite beam 2 line up vertically with the center of gravity of the transducer 1.

Several variants of the piezoelectric materials are shown in FIGS. 2A, 2B and 2C. In one embodiment as shown in FIG. 2A, the piezoelectric materials are thin rectangular plates 10 and 11 having surface electrodes 10a, 10b and 11a, 11b and been polarized along thickness directions. The piezoelectric plates are bonded to the substrate 3 through bonding layers 20 and 21. There may be additional encapsulation layers 30 and 31 applied on the outer electrodes 10a and 11b to insulate the transducer from surrounding fluid. In a second embodiment, the surfaces of the piezoelectric plates 12 and 13 may have stripped electrodes, where every other parallel electrode pairs are connected as 12a, 12b, 13a and 13b. The polarities of the voltages applied to the adjacent electrode pairs are opposite. The piezoelectric plates can therefore be tangentially polarized along the length directions. The piezoelectric plates are bonded to the substrate through bonding layers 22 and 23. There may also be encapsulation layers 32 and 33 on the outer surfaces for electric insulation. The said embodiment has merits of higher effective electromechanical coupling. In a third embodiment, piezoelectric plates 14 and 15 maybe assembled by bonding multiple piezoelectric segments at their electrode surfaces, which are then connected alternatively along the length direction as 14a, 14b, 15a and 15b. The polarities of the voltages applied to the adjacent electrodes are opposite. The piezoelectric plates can be polarized along the length directions. The piezoelectric plates are bonded to the substrate through bonding layers 24 and 25 and may also have encapsulation layers 34 and 35 on the outer surfaces for electric insulation. The said embodiment has merits of even higher effective electromechanical coupling.

Figure 3:
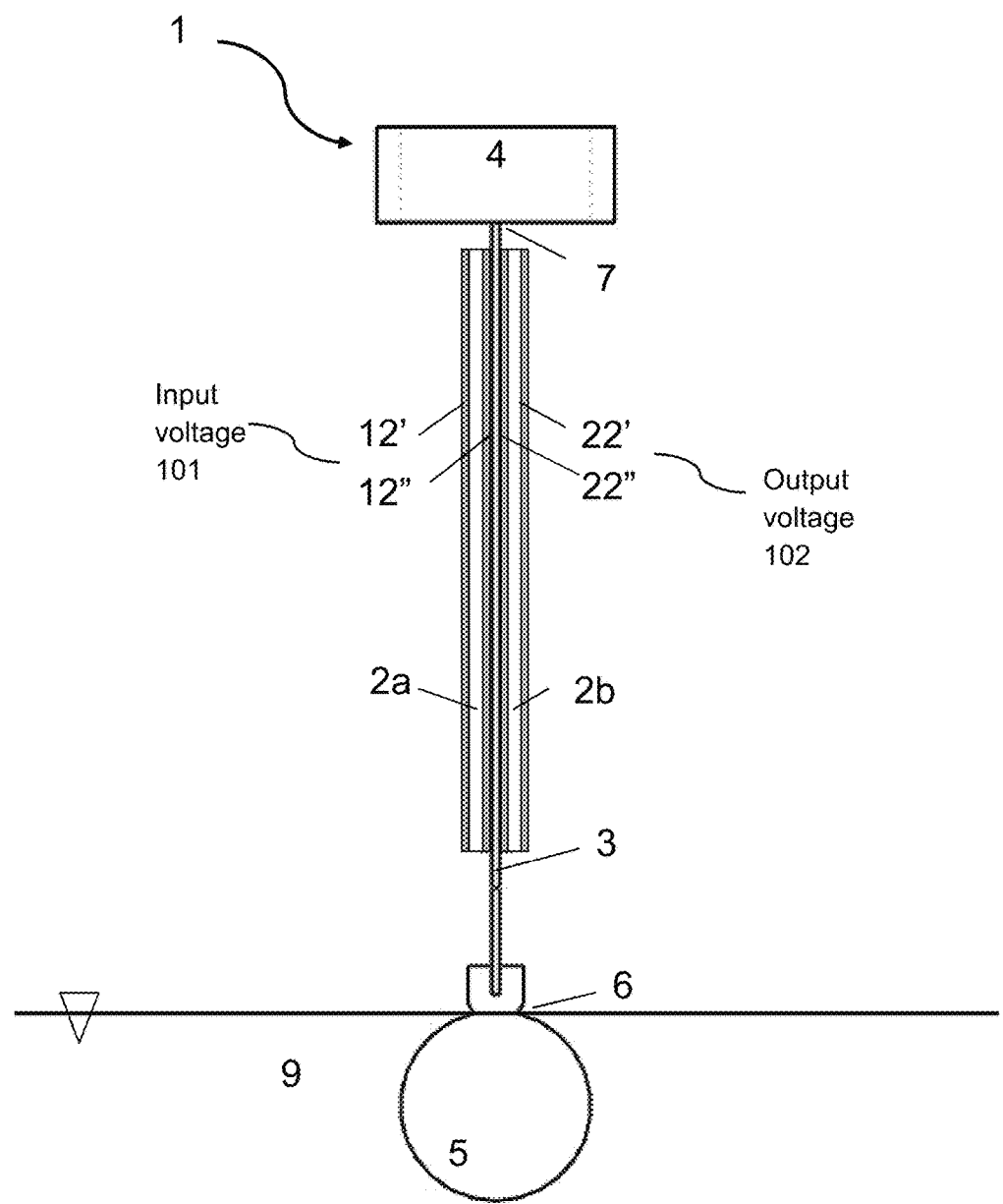
FIG. 3 illustrates one operation of the electromechanical transducer for measuring fluid viscosity.

In the present embodiment shown in FIG. 3, one of the two piezoelectric materials 2a, termed as actuator, may be driven by an input voltage 101 through its electrodes 12' and 12" to excite bending vibration of the composite beam 2 with an amplitude anti-node at the end of the sensor plate 5. Vibrations in other directions are restricted since the rigidities of the composite beam in other directions are significantly larger. The sensor plate 5 is immersed in the testing fluid 9 with fluid surface levels with recess 6. The fluid 9 is excited into shear oscillation due to the vibration of sensor plate 5. The friction force acted on the surfaces of the said sensor plate is proportional to the square root of the viscosity of the testing fluid 9. This friction force results in a vibration reduction of the composite beam 2. The vibration amplitude of the composite beam may be measured by the induced electrical voltage 102 from the second piezoelectric material 2b through its electrode 22' and 22", hence termed as receiver. This output voltage 102 decreases monotonically with increasing viscosity of the testing fluid 9.

Figure 4:
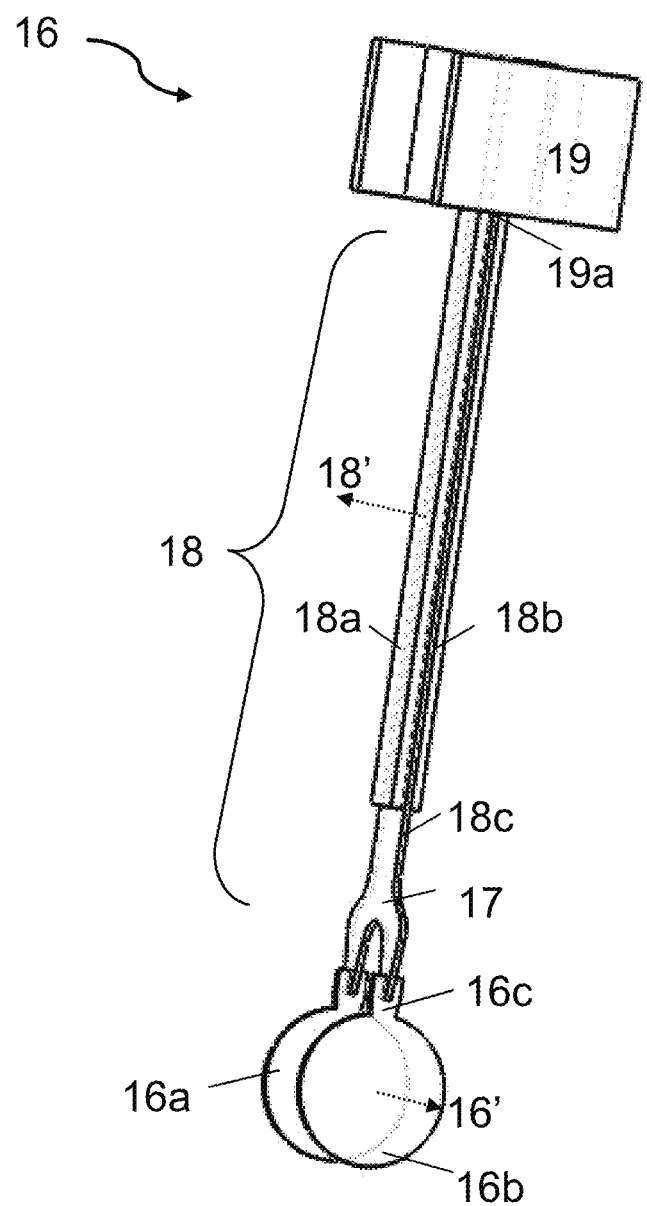
FIG. 4 illustrates a perspective view of another embodiment of the electromechanical transducer with improved sensitivity for low viscosity measurement.

FIG. 4 illustrates a perspective view of another embodiment of the electromechanical transducer 16. Multiple sensor plates 16a and 16b, having surface dimension significantly larger than the thickness, may be brazed or welded to the distal end 17 of a composite beam 18. The normal directions 16' of the surfaces of the said sensor plates are orthogonal to the normal direction 18' of the composite beam and the mass of the said sensor plates are preferably smaller than the mass of the composite beam. The said sensor plates may have identical recesses 16c that are flushes with the surface of the fluid. The composite beam 18 comprises of a thin metal substrate 18c with two electromechanical transduction materials, for example piezoelectric plates, 18a and 18b bonded to its surfaces. The piezoelectric plates can be one of the three variants as described as in FIG. 2. At proximal end 19a, the composite beam 18 is brazed or welded onto a supporting structure 19 whose stiffness and mass are significantly larger than that of the composite beam. The said sensor plates 16a and 16b may be made from the same metal material as the substrate 18c. Alternatively, they may be made from a specialty alloy that is chemically inert to the testing fluid. The center gravity of the sensor plates 16a and 16b are symmetric with respect to the center of gravity of the transducer 16. In this embodiment, by increasing the sensor plate surface area, the said transducer has merit of improved sensitivity to fluid of low viscosity.

Figure 5:
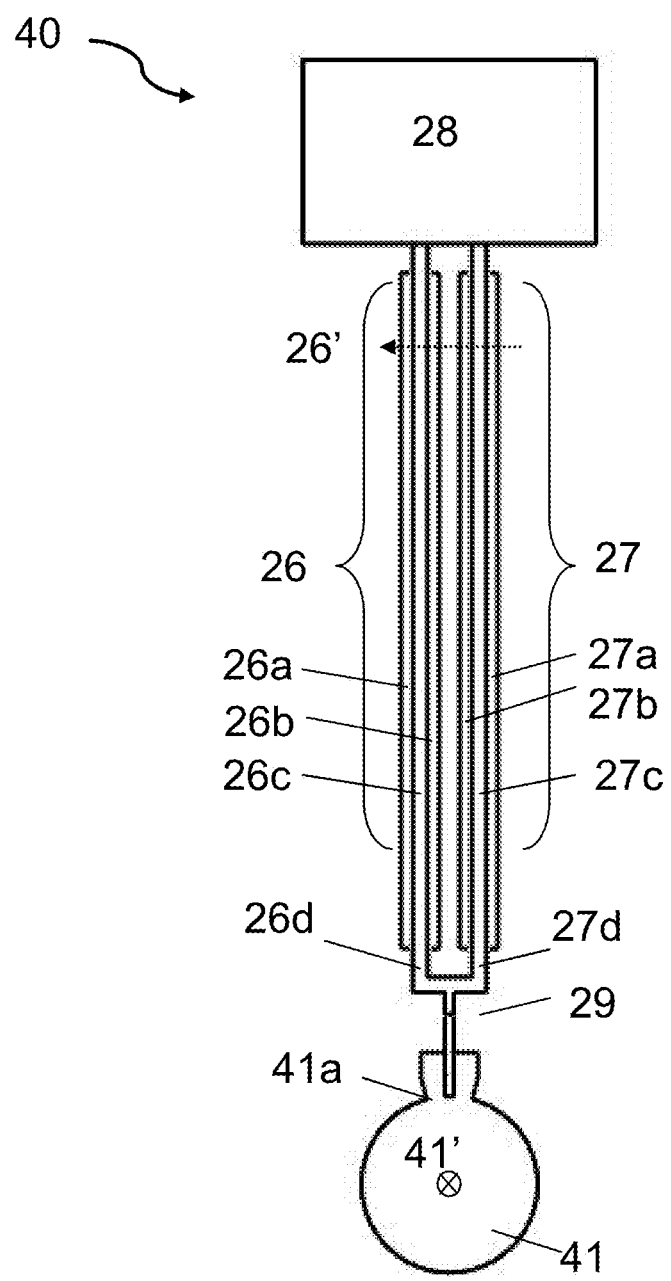
FIG. 5 illustrates a side view of another embodiment of the electromechanical transducer with improved sensitivity for medium to high viscosity measurement.

FIG. 5 illustrates a side view of another embodiment of the electromechanical transducer 40 comprising two composite beams 26 and 27. Each composite beam may comprise of a metal substrate 26c and 27c with two electromechanical transduction materials, for example piezoelectric plates, 26a, 26b and 27a, 27b bonded to its surfaces respectively. The piezoelectric plates can be one of the three variants as described as in FIG. 2. The two composite beams 26 and 27 are equal in lengths and are parallel to each other with same surface normal direction 26'. The width of each composite beam is appreciably larger than its thickness. At one ends the said composite beams are brazed or welded to a common supporting structure 28 whose stiffness and mass are significantly larger than the composite beams. The other ends of the composite beams 26d and 27d are connected via a light, stiff connector 29 with at least one sensor plate 41 attached to it. The connector 29 ensures the vibrations of the composite beams at their respective end 26d and 27d are in phase with the sensor plate 41. The said sensor plate may have surface dimension significantly larger than its thickness. The mass and size of the sensor plate is preferably smaller than the mass and size of the composite beams. The normal direction of the plate surface 41' is orthogonal to the normal direction of the surface of the composite beams 26'. The sensor plate 41 may have a recess 41a that flushes with the surface of the fluid. The sensor plate 41 may be made from a specialty alloy that is chemically inert to the testing fluid. The center of gravity of the sensor plate 41 lines up vertically with the center of gravity of the transducer 40. The centers of gravity of the composite beams 26 and 27 are symmetric with respect to the center of gravity of the transducer 40.

Figure 6:
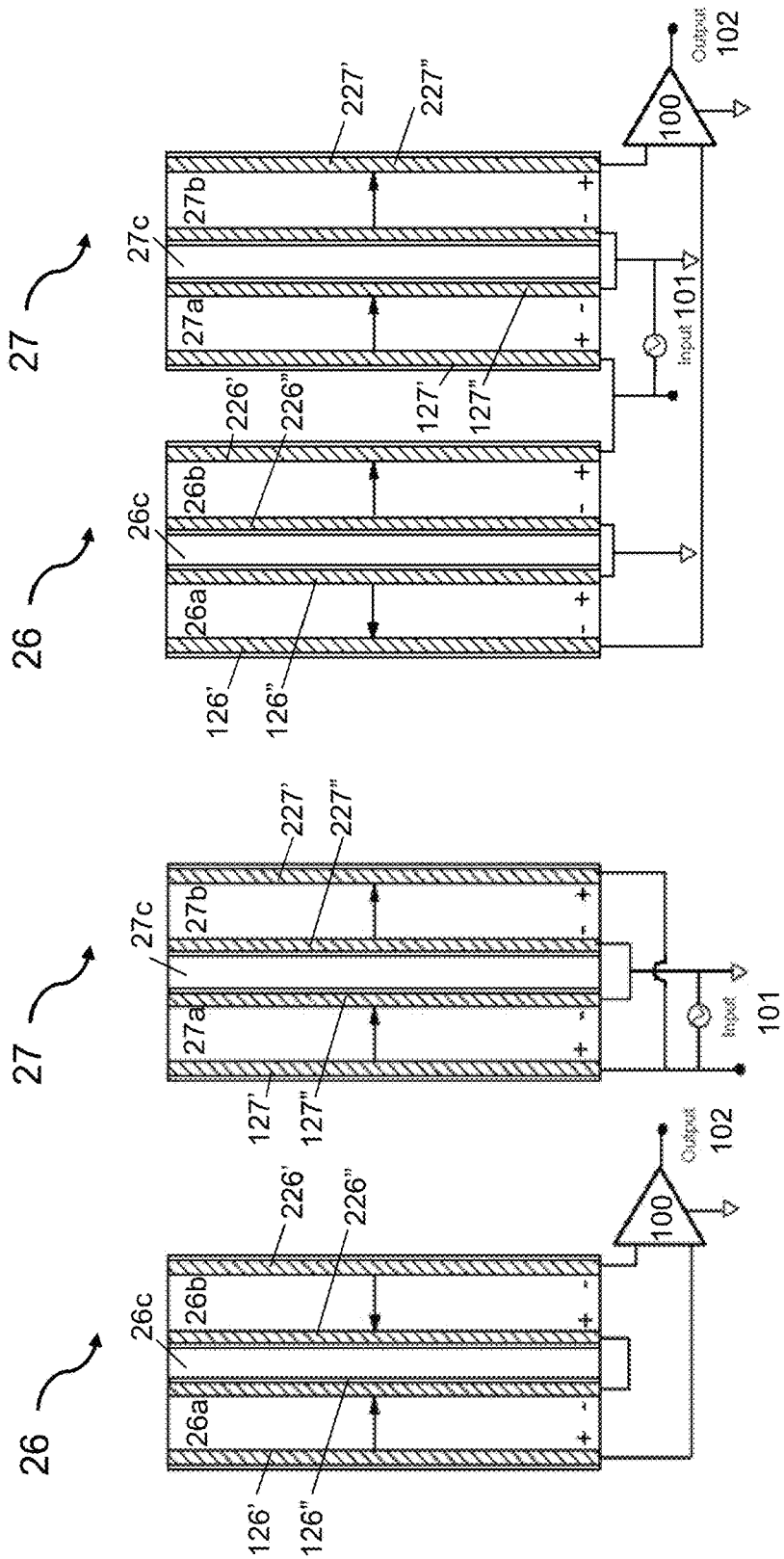
FIGS. 6A and 6B illustrate two embodiments of the electric configurations of the electromechanical transducer of FIG. 5.

FIGS. 6A and 6B illustrate two variants of the electrical connections of the electromechanical transducer 40. In one embodiment as illustrated in FIG. 6A, one of the composite beams 27 is used as actuator while the other composite beam 26 is used as receiver. The actuator 27 has two piezoelectric plates 27a and 27b been polarized in the same directions through electrodes 127', 127" and 227', 227" respectively. An input voltage 101 is supplied through terminals of 127' (been connected with 227') and 127" (been connected with 227"). In such case, the piezoelectric plates 27a and 27b are electrically connected in parallel. The receiver 26 has two piezoelectric plates 26a and 26b been polarized in the opposite directions through electrodes 126', 126" and 226', 226" respectively. The output voltage 102 is obtained through terminals of 126' and 226", while 126" and 226' are electrically connected. In such case, the piezoelectric plates 26a and 26b are electrically connected in series. The output voltage 102 may be fed into a differential amplifier 100 for further processing. In the second embodiment as illustrated in FIG. 6B, the piezoelectric plates 26b and 27a are used as actuator with the same polarization direction. The input voltage 101 is supplied between electrodes 226' (been connected with 127') and 226" (been connected with 127"). In such case 26b and 27a are electrically connected in parallel. The piezoelectric material 26a and 27b are used as receiver with polarization direction been opposite with respect to each other. The output voltage 102 is obtained through terminals of 126' and 227'. In such case, the piezoelectric plates 26a and 27b a are electrically connected in series. The output voltage 102 may be fed into a differential amplifier 100 for further processing.

Figure 2:
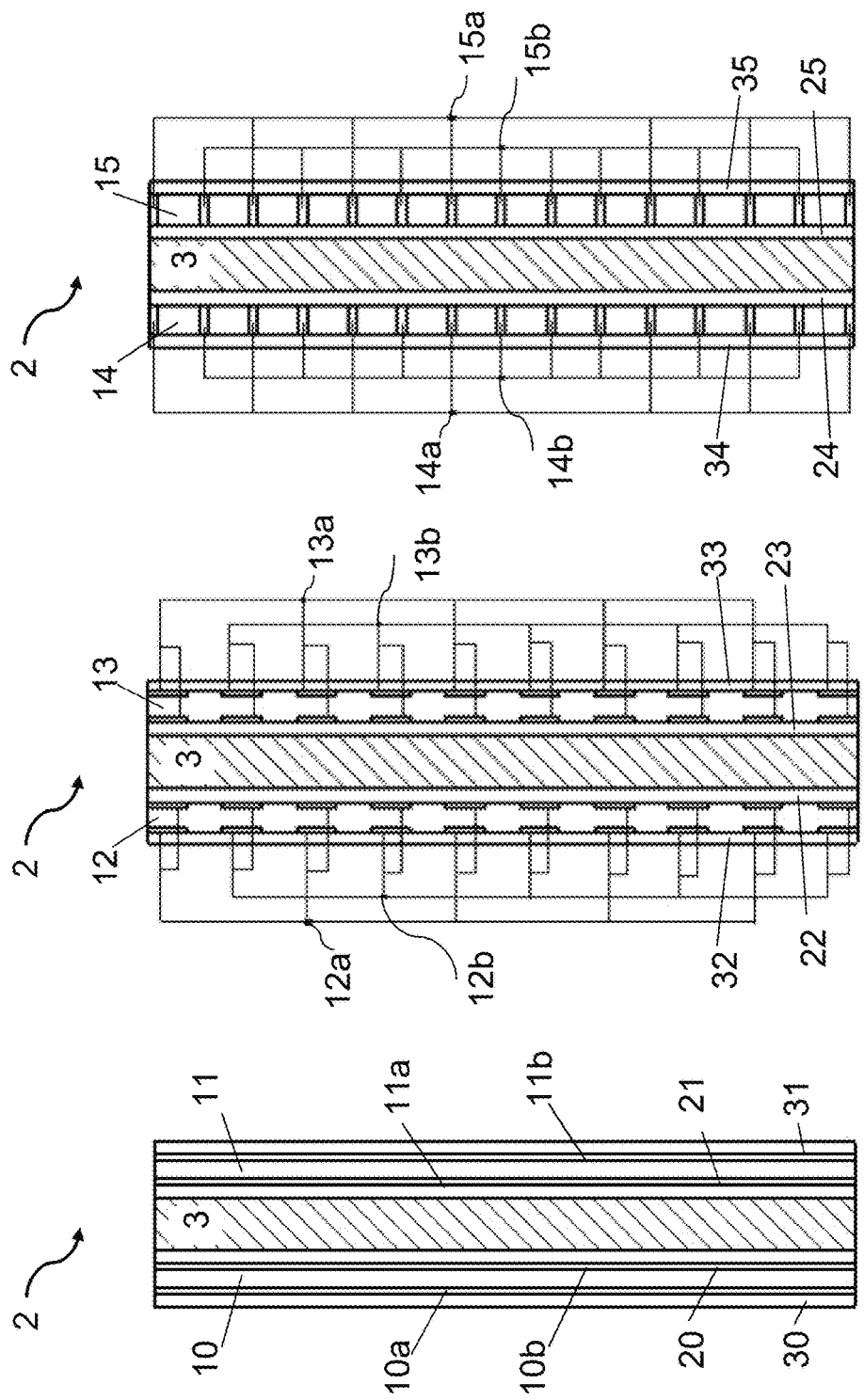
FIGS. 2A, 2B and 2C illustrate three variants of the electromechanical transduction materials.

The piezoelectric plates polarizations described in the current embodiments are illustrative and shall apply to the variants of the piezoelectric material assemblies in FIG. 2. Despite different embodiments of the electrical configurations, the circuitry functions the same. The actuator is driven by a voltage input to excite bending vibration of the composite beams with vibration amplitude anti-node at the end of the sensor plate. Vibrations in other directions are restricted since the rigidities of the composite beams in other directions are significantly larger. The fluid is driven into shear oscillation around the sensor plate. The friction force acted on the surface of the sensor plate increases as the viscosity of the testing fluid increases, which results in a vibration reduction of the composite beams. The level of the vibration amplitude is measured by the receiver, which is connected to a differential amplifier and then possibly a signal conditioning circuit. The output voltage of the receiver decreases monotonically with increasing in fluid viscosity and may be used to measure the viscosity of the testing fluid. The electromechanical transducer 40 with the disclosed embodiments of electrical connections has the merit of doubling the input power and the receiving sensitivity. It may be used for fluid with medium to higher viscosity.

Figure 7:
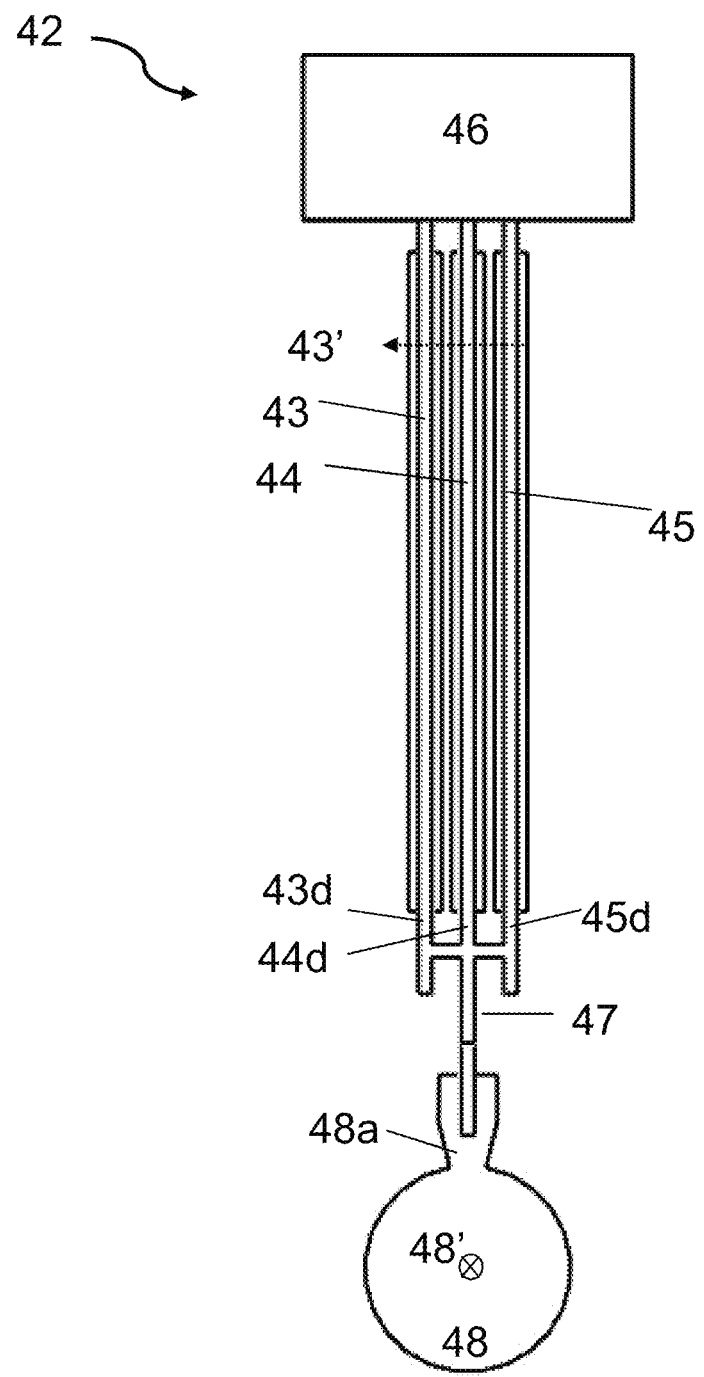
FIG. 7 illustrates a side view of another embodiment of the electromechanical transducer with further improved sensitivity for medium to high viscosity measurement.

FIG. 7 illustrates a side view of another embodiment of the electromechanical transducer 42. Here, multiple composite beams, for example 43, 44, 45 of equal lengths may be attached to a common support structure 46 whose mass and stiffness are significantly larger than the composite beams. The width of each composite beam is appreciably larger than its thickness. A light, stiff connector 47 connects the three said beams at their distal ends of 43d, 44d and 45d with at least one sensor plate 48 attached to it. The connector 47 ensures the vibrations of the composite beams at their distal ends are in phase with the sensor plate 48. The sensor plate has a surface dimension significantly larger than its thickness with a mass preferably smaller than the composite beams. Each composite beam is comprised of a metal substrate with two electromechanical transduction materials, for example piezoelectric plates, bonded to their surfaces. The said composite beams are parallel to each other, with surface normal direction 43' been orthogonal to the surface normal direction 48' of the sensor plate 48. The sensor plate 48 may have a recess 48a that is flush with the surface of the fluid. The sensor plate 48 may be made from the same material as the metal substrates of the composite beams. Alternatively, it may be made from a specialty alloy that is chemically inert to the testing fluid. The center of gravity of the sensor plate 48 and the composite beams 43, 44, 45 lines up vertically with the center of gravity of the device 42.

Figure 8:
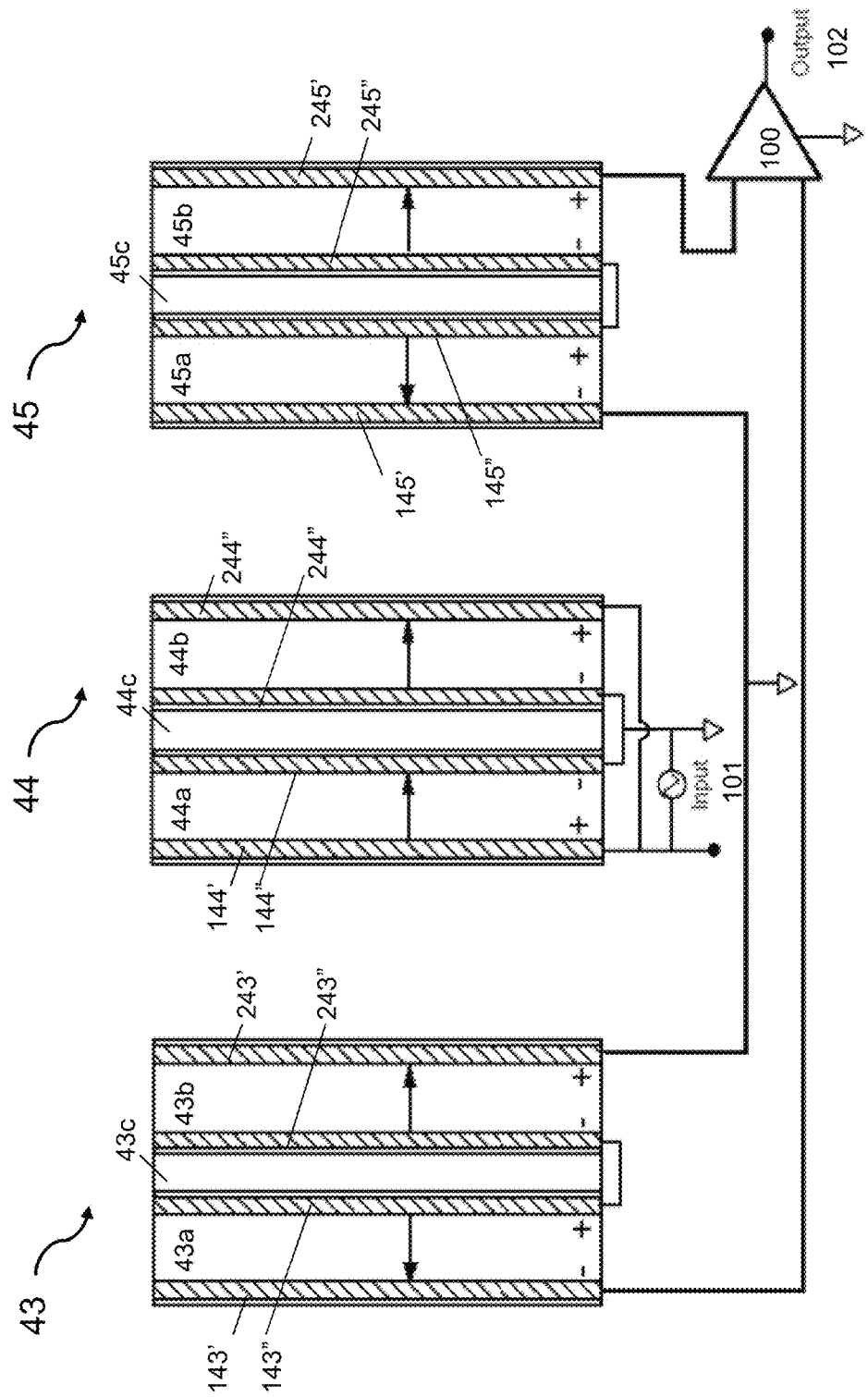
FIG. 8 illustrates one embodiment of the electric configuration of the electromechanical transducer in FIG. 7.

FIG. 8 illustrate one embodiment of electrical connection for the electromechanical transducer 42. One composite beam 44 comprises of two piezoelectric plates 44a and 44b with same polarizations, bonded to the substrate 44c, is used as actuator. The input voltage 101 is supplied between electrodes 144' (been connected to 244') and 144" (been connected to 244"). In such case, the piezoelectric materials 44a and 44b are connected in parallel. The composite beams 43 and 45, each comprises of two piezoelectric plates of 43a, 43b and 45a, 45b, bonded to their respective substrate 43c and 45c, are used as receiver. On each composite beam, the polarizations of the two piezoelectric plates are opposite to each other. Their output voltages are connected in series. For example, the electrodes 143" and 243" of the composite beam 43 are connected, while the output voltage is taken from 143' and 243'. The output voltages 102 from the composite beams of and 45 are connected in series to a differential amplifier 100 for further processing.

Figure 9:
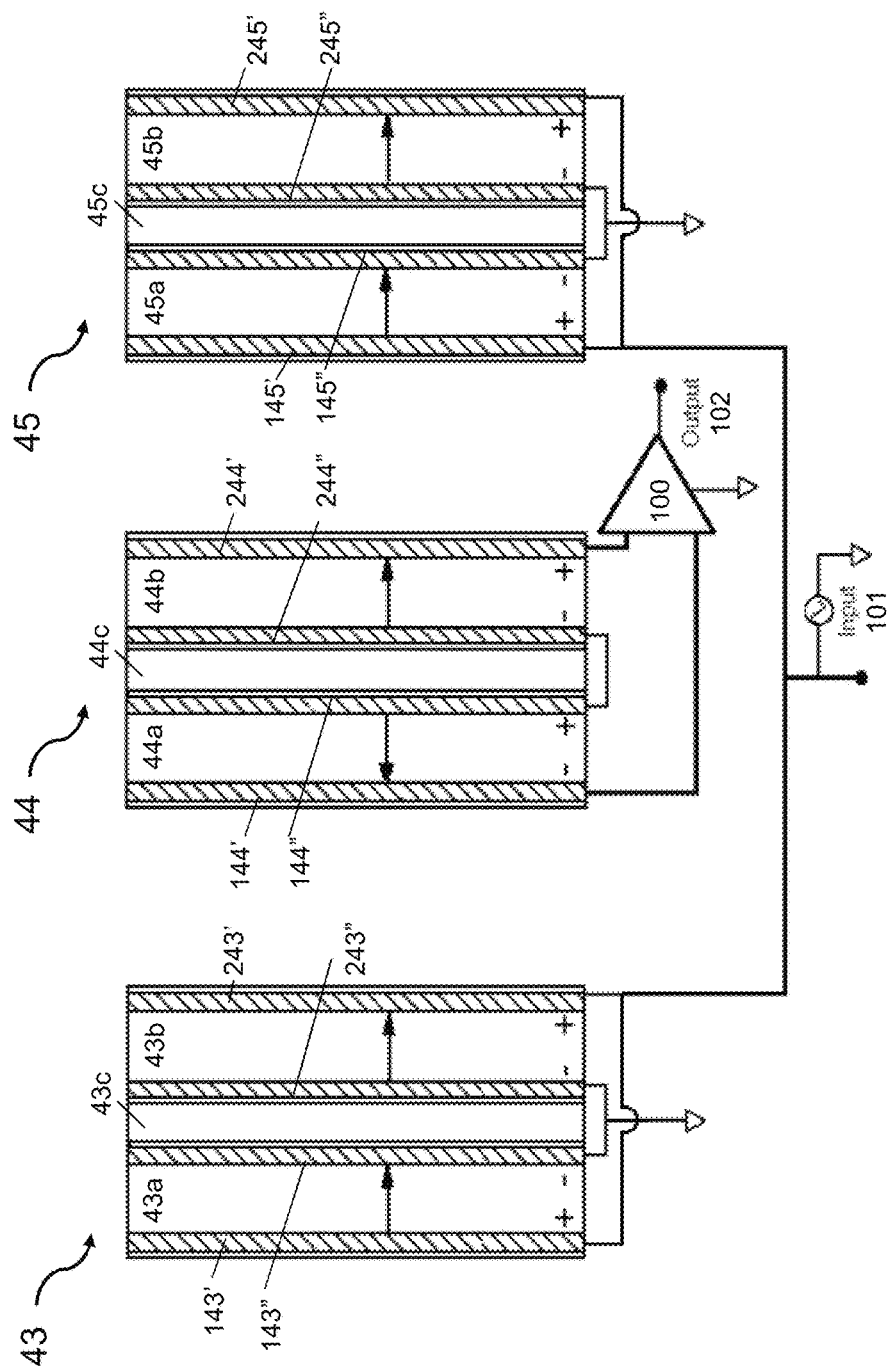
FIG. 9 illustrates another embodiment of the electric configuration of the electromechanical transducer in FIG. 7.

FIG. 9 illustrate another embodiment of electrical connection for the electromechanical transducer 42. The composite beams 43 and 45, each of which comprise of two piezoelectric plates of the same polarizations, are used as actuator. The composite beams 43 and 45 are electrically connected in parallel. In such case, electrodes 143', 243', 145' and 245' are connected to serve as one terminal of the input voltage 101. Electrodes 143", 243", 145" and 245" are connected together to serve as the other terminal for input voltage 101. The third composite beam 44, comprises' of two piezoelectric plates of opposite polarizations is used as receiver. The electrodes 144" and 244" are connected and the output voltage 102 is taken between 144' and 244'.

The piezoelectric plates polarizations described in the disclosed embodiments are illustrative and shall apply to the variants of the piezoelectric material assemblies in FIG. 2. Despite difference on the embodiments of the electrical configurations, the circuitry functions the same. The actuator is driven by a voltage input to excite bending vibration of the composite beams with vibration amplitude anti-node at the end of the sensor plate. Vibrations in other directions are restricted since the rigidities of the composite beams in other directions are significantly larger. The fluid is driven into shear oscillation around the sensor plate. The friction force acted on the surfaces of the sensor plate increases as the viscosity of the testing fluid increases, which results in a vibration reduction of the composite beams. The level of the vibration amplitude is measured by the receiver, which is connected to a differential amplifier and maybe followed by a signal conditioning circuit. The output voltage of the receiver decreases monotonically with increasing in fluid viscosity and may be used to measure the viscosity of the testing fluid. The electromechanical transducer 42 with the disclosed embodiments of the electrical configurations have the merit of further improved excitation power and improved receiving sensitivity that maybe be used for fluid with medium to higher viscosity.

Figure 10:
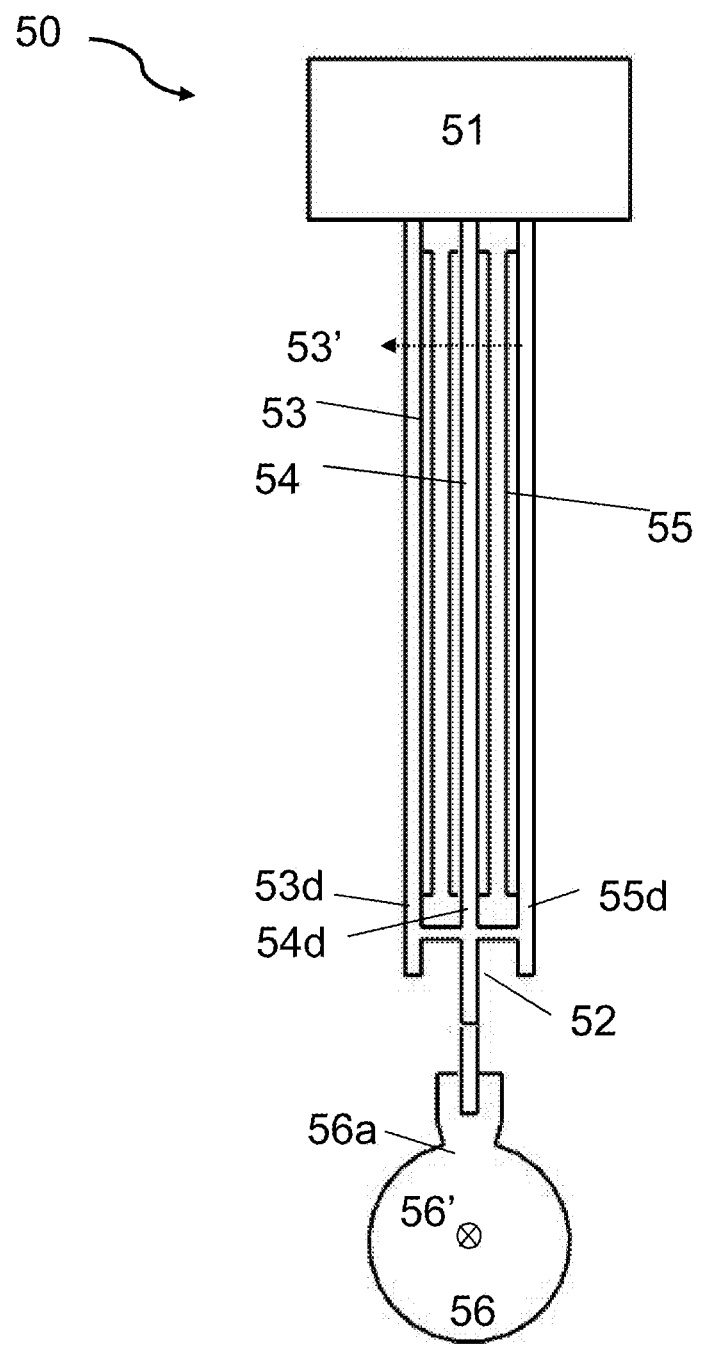
FIG. 10 illustrates a side view of another embodiment of the electromechanical transducer with improved sensitivity for medium to high viscosity measurement.

FIG. 10 illustrates a side view of another embodiment of the electromechanical transducer 50. Here, three beams, 53, 54, 55 of equal lengths may be attached to a common support structure 51 whose stiffness and mass are significantly larger than the composite beams. The width of each composite beam is appreciably larger than its thickness. A stiff connector 52 connects the three beams at their distal ends of 53d, 54d and 55d with at least one sensor plate 56 attached to it. The connector 52 ensures the vibrations at the composite beams at their distal ends are in phase with the sensor plate 56. The sensor plate has a surface dimension significantly larger than its thickness and with a mass preferably smaller than the composite beams. Each composite beam is comprised of a metal substrate with at least one electromechanical transduction materials, for example piezoelectric plates, bonded to their surfaces. The said composite beams are parallel to each other, with surface normal direction 53' been orthogonal to the surface normal direction 56' of the sensor plate 56. The sensor plate 56 may have a recess 56a that is flush with the surface of the fluid. The sensor plate 56 may be made from the same material as the metal substrates of the composite beams. Alternatively, it may be made from a specialty alloy that is chemically inert to the testing fluid. The center of gravity of the sensor plate 56 and composite beams 53, 54, 55 should line up vertically with the center of gravity of the transducer 50.

Figure 11:
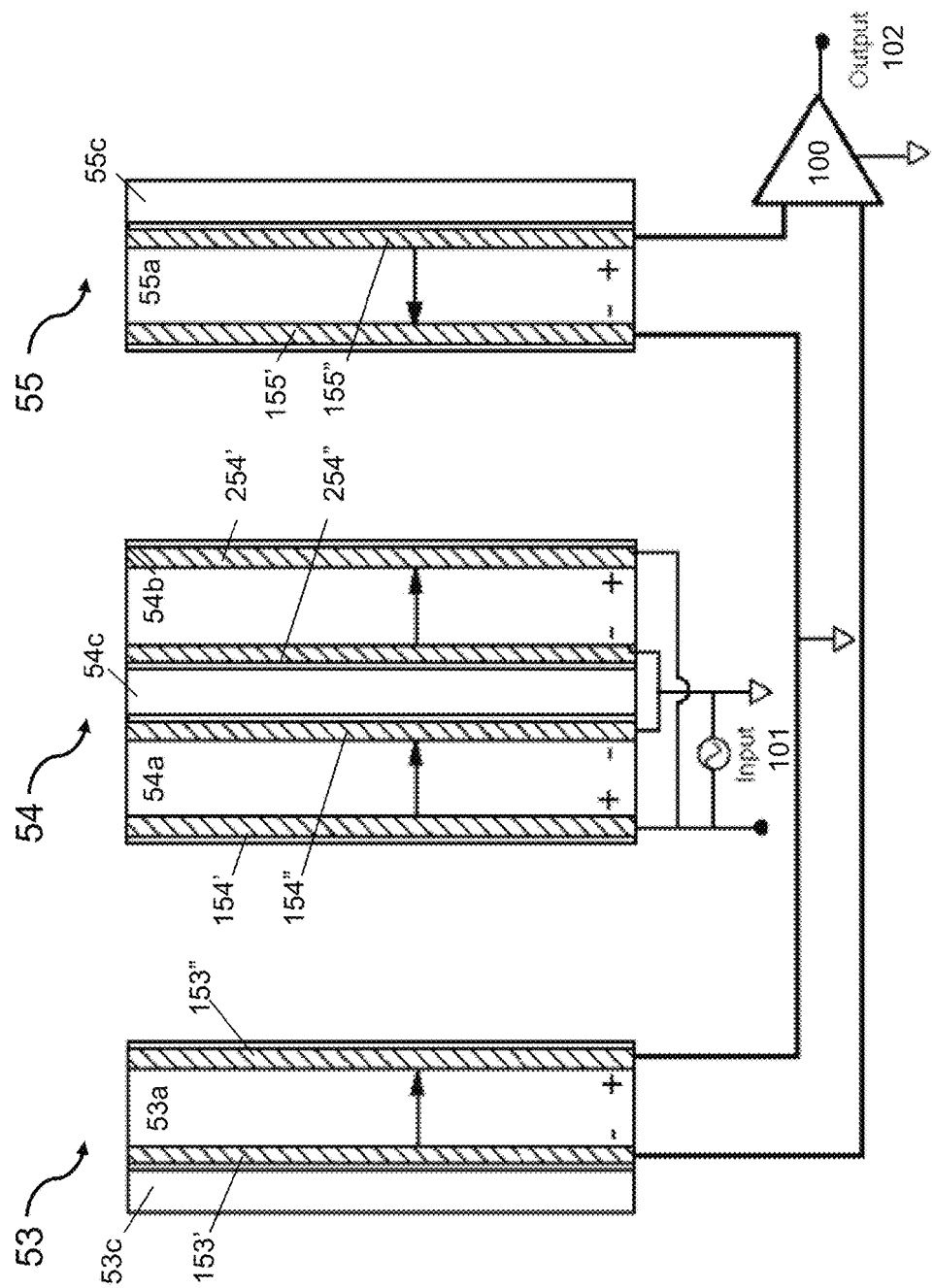
FIG. 11 illustrates one embodiment of the electric configuration of the electromechanical transducer in FIG. 10.

FIG. 11 illustrate one embodiment of electrical connection for the electromechanical transducer 50. The composite beam 54 comprises of two piezoelectric plates 54a and 54b with same polarizations, bonded to the substrate 54c, is used as actuator. The input voltage 101 is supplied between electrodes 154' (been connected to 254') and 154" (been connected to 254"). In such case, the piezoelectric plates 54a and 54b are connected in parallel. The composite beams 53 and 55, each comprises of one piezoelectric plate of 53a and 55a bonded to their respective substrate 53c and 55c, are used as receiver. 53a and 55a are polarized opposite to each other. The output voltages 102 are obtained through electrodes 153' and 155" with 153" and 155' been connected together. In such case, the output voltage from 53 and 55 are connected in series. The output 102 is followed by a differential amplifier 100 for further processing.

Figure 12:
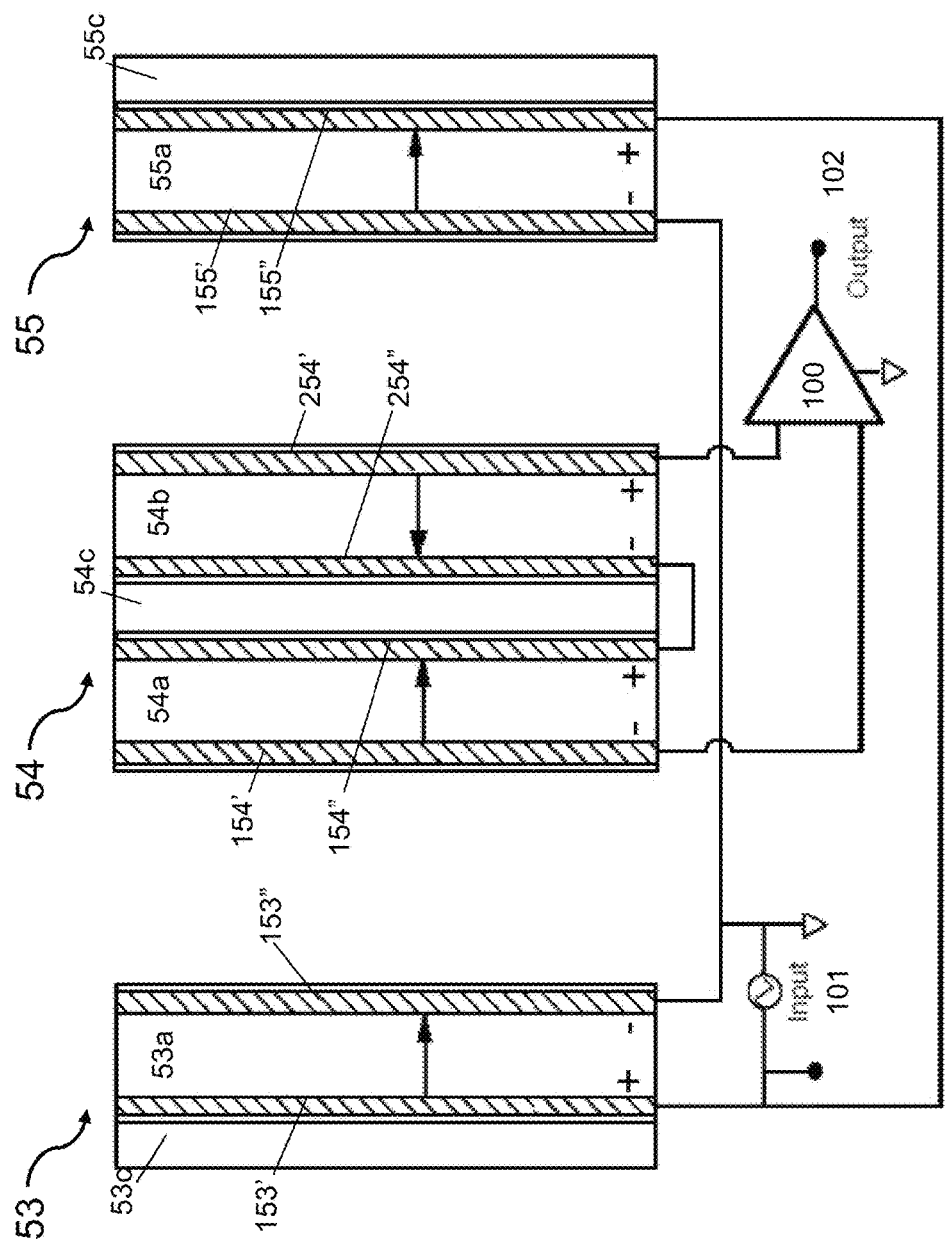
FIG. 12 illustrates another embodiment of the electric configuration of the electromechanical transducer in FIG. 10.

FIG. 12 illustrates another embodiment of electrical connection for the electromechanical transducer 50. The composite beams 53 and 55, each of which comprises of one piezoelectric plate 53a and 55a with the same polarizations, are electrically connected in parallel to be used as actuator. The composite beam 54 comprises of two piezoelectric plates 54a and 54b with opposite polarizations are connected in series to be used as receiver.

The piezoelectric plates polarizations described in the disclosed embodiments are illustrative and shall apply to the variants of the piezoelectric material assemblies in FIG. 2.

Despite difference on the embodiments of the electrical configurations, the circuitry functions the same. The actuator is driven by a voltage input to excite bending vibration of the composite beams with vibration amplitude anti-node at the end of the sensor plate. Vibrations in other directions are restricted since the rigidities of the composite beams in other directions are significantly larger. The fluid is driven into shear oscillation around the sensor plate. The friction force acted on the surfaces of the sensor plate increases as the viscosity of the testing fluid increases, which results in a vibration reduction of the composite beams. The level of the vibration amplitude is measured by the receiver, which is connected to a differential amplifier and maybe followed by a signal conditioning circuit. The output voltage of the receiver decreases monotonically with increasing in fluid viscosity and may be used to measure the viscosity of the testing fluid. The electromechanical transducer 50 with the disclosed embodiments of the electrical configurations have the merit of improved excitation power and improved receiving sensitivity that maybe be used for fluid with medium to higher viscosity.

Figure 13:
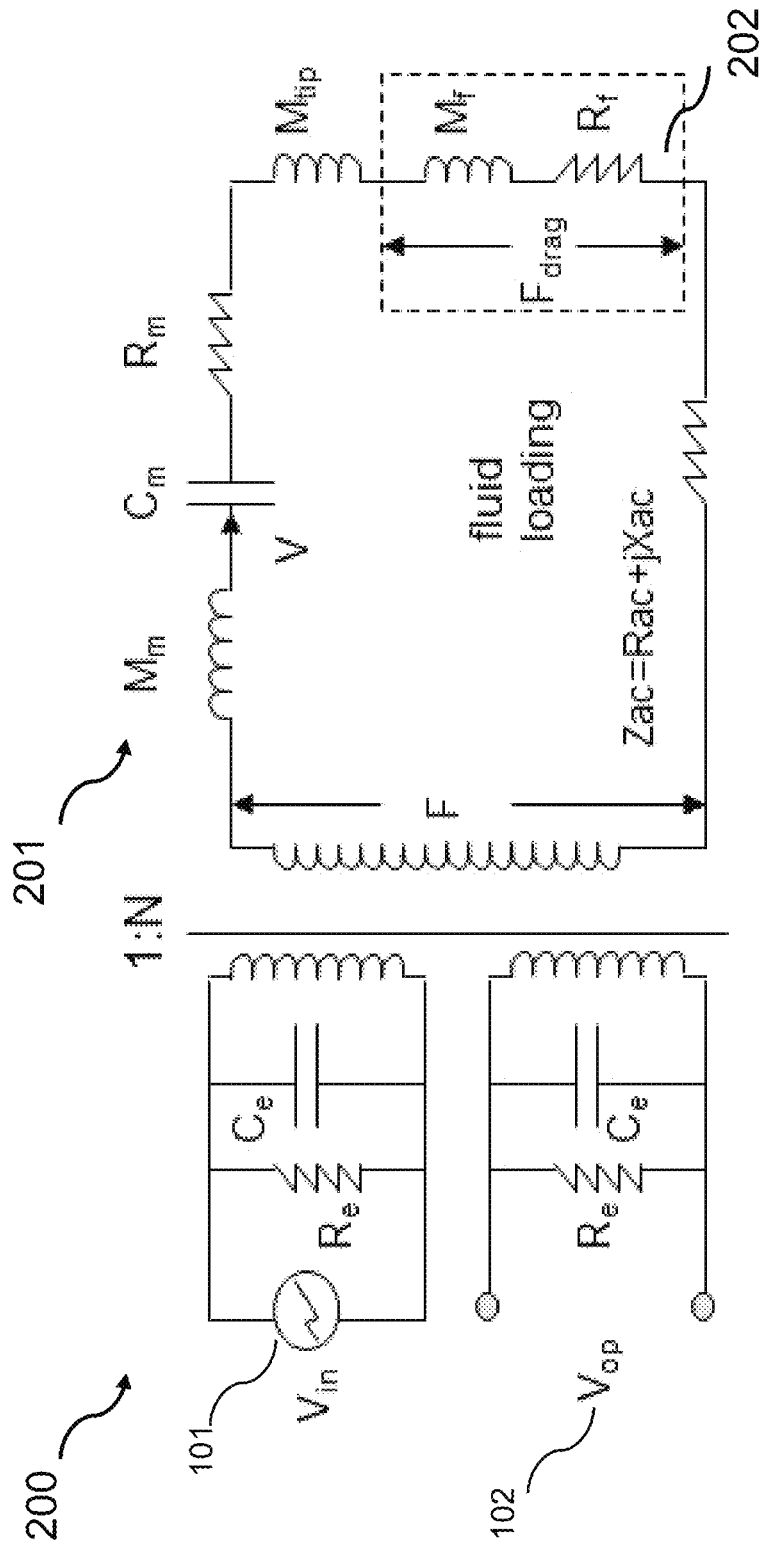
FIG. 13 illustrates an electro-mechanical circuit representation of the electromechanical transducer using voltage response method.
Figure 14C:
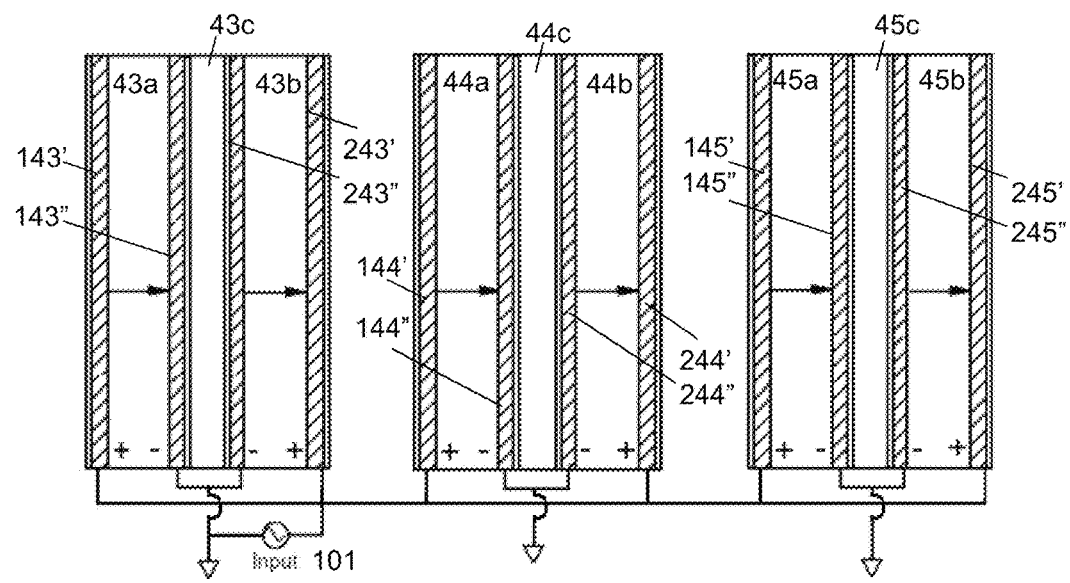
Figure 14D:
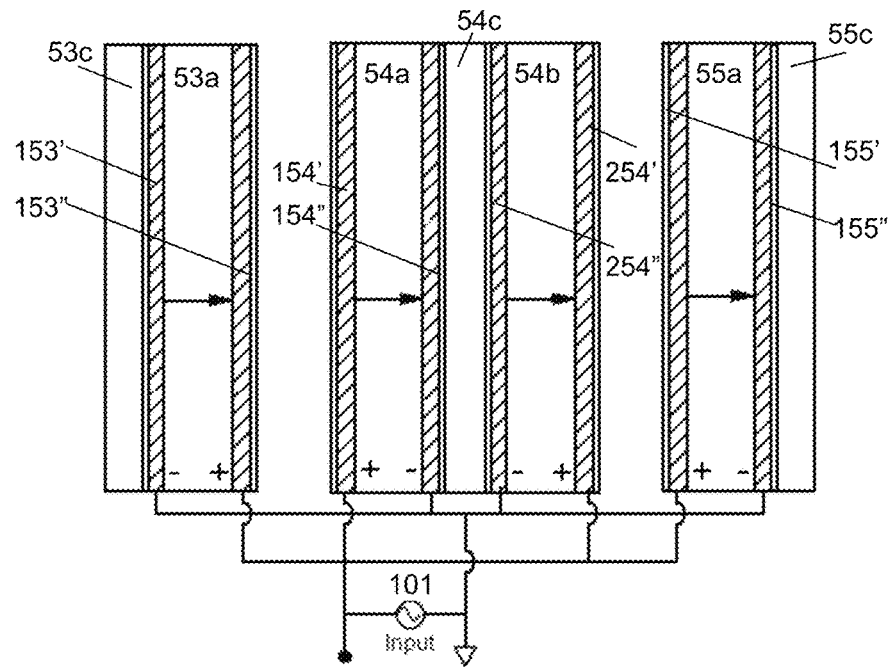

FIG. 13 illustrates an electro-mechanical circuit representation of electromechanical transducer employing voltage response method. The electromechanical transducer may refer to the transducer 1, 16, 40, 42, 50. In voltage response method, one (or a set of) piezoelectric plate(s) is used as actuator with an input voltage 101, represented as Vin. The other (or a set of) piezoelectric plate(s) is used as receiver whose open circuit voltage 102 is represented as Vop. The electrical branch 200 of the circuit represents the electrical characteristics of the electromechanical transduction material, in particular, the piezoelectric material. The mechanical circuit 201 represents the mechanical load of the transducer under bending vibration. In the mechanical circuit 201, the parameters Mm, Cm, Rm represent equivalent mechanical mass, compliance and structural loss of the composite beam (s). Mtip represents the equivalent mass of the sensor plate(s). $M_f$ and $R_f$ represent mechanical impedance of fluid acting on the surface of the sensor plate(s), from fluid mechanics theory, it can be deduced that:

$$M_f = S\sqrt{\frac{\mu\rho}{2\omega}} \; ; \; R_f = S\sqrt{\frac{\rho\mu\omega}{2}} \; , \tag{1}$$

where S is the surface area of the sensor plate, $\rho$ and $\mu$ are density and dynamic viscosity of the fluid. $\omega$ is the angular frequency of the oscillation. The impedance Zac=Ra+jXa represents the equivalent acoustic radiation impedance of the composite beam(s) which is extremely small compared to either $M_f$ or $R_f$. The reference velocity V, which is the velocity at the distal end(s) of the composite beam(s), can be represented as:

$$V = \frac{NV_{in}}{\left(j\omega M_m + \frac{1}{j\omega C_m} + R_m + R_a + jX_a + j\omega M_{tip} + j\omega M_f + R_f\right)}, \tag{2}$$

where N represents the electromechanical transformation coefficient. The output open circuit voltage can be obtained from as:

$$V_{op} = NV\left(\frac{1}{j\omega C_e} // R_e\right) = NV\frac{R_e}{1 + jQ_e}, \tag{3}$$

The voltage response of the transducer in fluid is defined as:

$$F_f(f) = \frac{V_{op}}{V_{in}} = \frac{R_e}{1+jQ_e} \frac{N^2}{j\omega M_{beam} + \frac{1}{j\omega C_m} + R_{beam} + j\omega M_f + R_f}, \quad (4)$$

and its response in air is:

$$F_a(f) = \frac{V_{op}}{V_{in}} = \frac{R_e}{1+jQ_e} \frac{N^2}{j\omega M_{beam} + \frac{1}{j\omega C_m} + R_{beam}}, \quad (5)$$

where $M_{beam}=M_m+M_{tip}+X_d/\omega$, $R_{beam}=R_m+R_a$ and $Q_e$ is the electrical quality factor for piezoelectric material, which is typically around 100 for piezoelectric lead zirconate titanate. If to define the resonance $f_1$ corresponds to the 90° phase of the voltage response function, i.e. the reactance of the mechanical impedance is zero, one obtain:

$$F_f(f_1) = \frac{1}{j\omega_1 C_e} \frac{N^2}{R_{beam}(f_1) + R_f(f_1)}.$$

Similarly, at resonance $f_0$ in air, the voltage response function is:

$$F_a(f_0) = \frac{1}{j\omega_0 C_e} \frac{N^2}{R_{beam}(f_0)}.$$

Therefore one can obtain:

$$R_f = \left(\frac{f_0 F_a(f_0)}{f_1 F_f(f_1)} - \frac{R_{beam}(f_1)}{R_{beam}(f_0)}\right) R_{beam}(f_0) = S_{d1}\sqrt{\pi f_1 \mu \rho}, \quad (6)$$

$R_{beam}$ accounts for all the internal loss of the transducer, which is an instrument constant and can be determined by measuring the mechanical quality factor of the transducer in air or by calibrate the transducer from fluids with known density and viscosity. In addition, if considering the internal loss $R_{beam}(f)$ does not change over the resonant frequency, one can establish the relation of transducer voltage response function to the fluid property as:

$$\frac{f_0 F_a(f_0)}{f_1 F_f(f_1)} - 1 = \text{Constant}\sqrt{f_1 \mu \rho},$$

in the log scale this relation can be written as:

$$\log\left[\frac{f_0 F_a(f_0)}{f_1 F_f(f_1)} - 1\right] = \frac{1}{2}\log\left[f_1 \mu \rho\right] + \text{Constant}, \quad (7)$$

A similar relationship was also obtained by Woodward in his publication [Ref. J. G. Woodward, A vibrating-plate Viscoemeter, Journal of colloid Science, 01, 1953].

FIGS. 14A~14D illustrate variants of electrical connections for the electromechanical transducer employing conductance response method. The electromechanical transducer may refer to transducer 1, 16, 40, 42 and 50. In each embodiment, the piezoelectric plates are polarized in the same directions and are electrically connected in parallel. The electrical conductance of the transducer can be obtained from the input impedance measurement, which is well known to those skilled in the art.

Figure 15A:
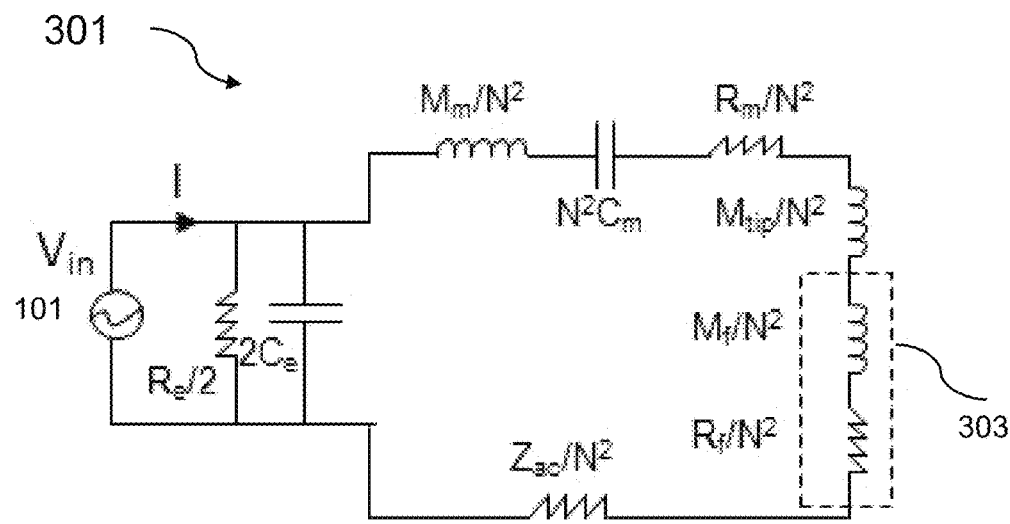
FIGS. 15A and 15B illustrate equivalent electro-mechanical circuit and a simplified equivalent electrical circuit of the electromechanical transducer using conductance response method.
Figure 15B:
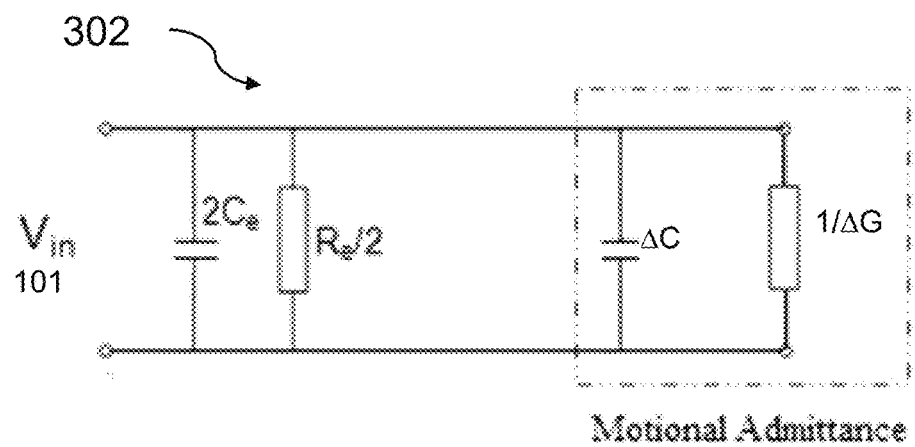

FIGS. 15A and 15B illustrate equivalent circuit representation of the electromechanical transducer employing conductance response method. Circuit 301 represents the electrical equivalent of the transducer with transformed mechanical load. The oscillation of fluid introduces additional mass and resistance to the mechanical circuit represented as 303. This load can be transformed into equivalent electrical circuit represented by 302 as an electrical capacitance of $\Delta C$ and conductance $\Delta G$. The conductance $\Delta G$ has mathematical relation to the viscosity of the fluid and can be measured to indicate the fluid viscosity.

Figure 16:
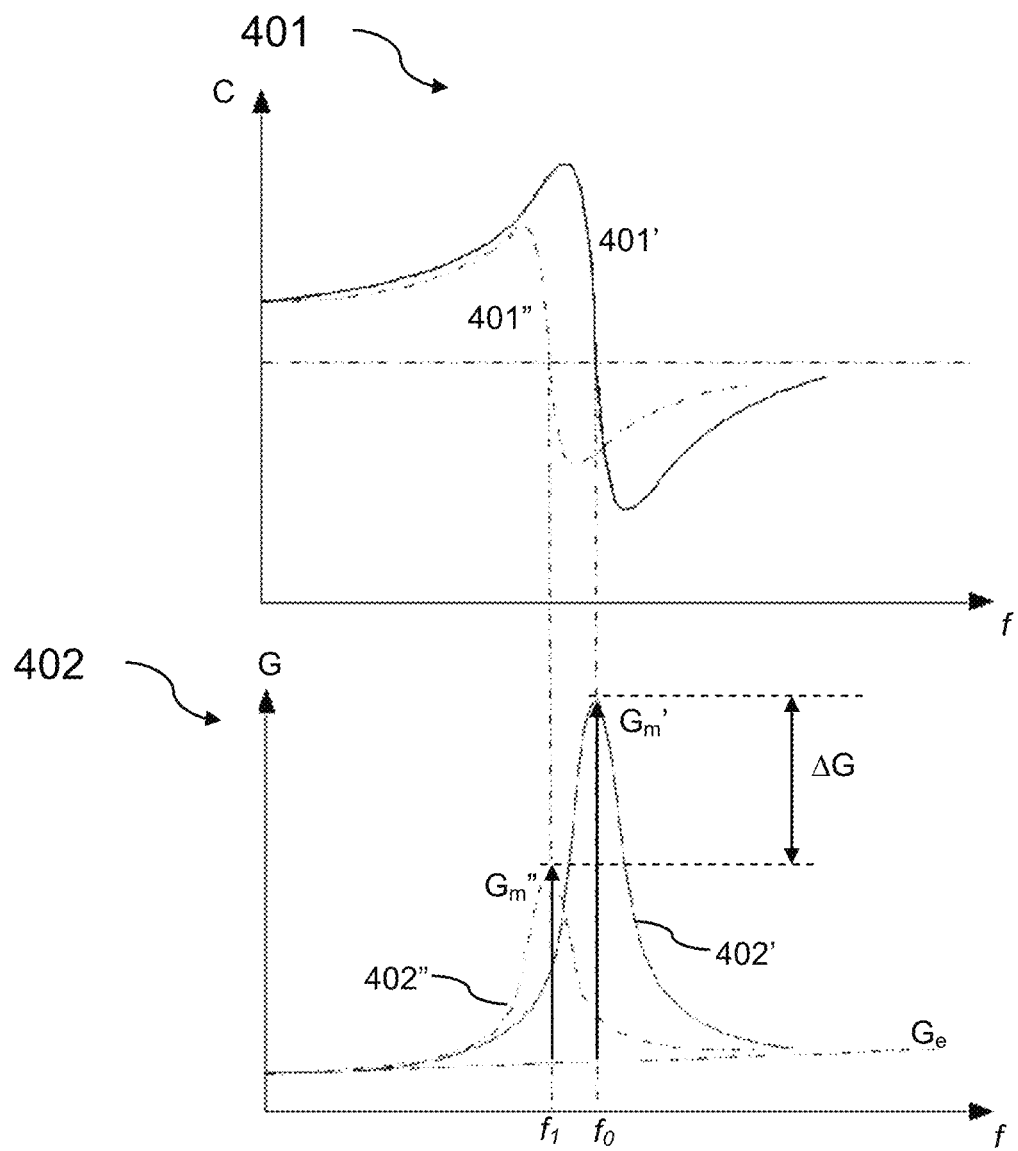
FIG. 16 illustrates the representative equivalent electrical capacitance and conductance curve of the electromechanical transducer operates in air and in fluid respectively.

FIG. 16 describes typical electrical capacitance curve 401 and conductance curve 402 vs frequencies for the electromechanical transducer operated in air as 401', 402' and in fluid as 401", 402" respectively. The peak on the conductance represents the resonant vibration of the transducer, of which $G=G_m+G_e$, where $G_e$ is the electrical loss of the piezoelectric material and $G_m$ is the mechanical conductance where at resonance, $G_e \ll G_m$. In air, at resonance $f_0$ the conductance is:

$$G^{air}(f_0) = G_e(f_0) + G'_m = G_e(f_0) + \frac{N^2}{R_{beam}(f_0)},$$

where $R_{beam}(f_0)$ accounts for internal structural loss and radiated acoustic resistance of the transducer. In fluid, at resonance $f_1$ the conductance is:

$$G^{fluid}(f_1) = G_e(f_1) + \frac{N^2}{R_f(f_1) + R_{beam}(f_1)},$$

where $R_f(f_1)$ accounts for frictional force from the fluid. Since the electric loss line $G_e(f)$ and internal loss of the transducer $R_{beam}(f)$ have little changes over the frequency range from $f_0$ to $f_1$ the change of conductance is primarily due to the frictional force from the fluid. The following relation can be obtained:

$$\frac{G^{air}(f_0)}{G^{fluid}(f_1)} - \frac{R_{beam}(f_1)}{R_{beam}(f_0)} \approx \frac{G^{air}(f_0)}{G^{fluid}(f_1)} - 1 = \frac{R_f(f_1)}{R_{beam}(f_0)}, \quad (8)$$

$$R_{beam}(f_0) \approx \frac{N^2}{G^{air}(f_0)},$$

$N^2$ and $R_{beam}(f_0)$ are instrument constants and may be obtained through calibration from a fluid with known density and viscosity. Therefore one may obtain:

$$\log\left[\frac{G_m^{air}(f_0)}{G_m^{fluid}(f_1)} - 1\right] = \log(S_{d1}\sqrt{\pi f_1 \mu \rho}) = \frac{1}{2}\log[f_1 \mu \rho] + \text{Constant}, \quad (9)$$

Equation (9) describes the relation between conductance of the transducer with viscosity and density of the fluid.

EXAMPLES

Viscosity Measurement Using Voltage Response Method

This example demonstrates the development of a prototype transducer employing voltage response method for viscosity measurement. The transducer comprises two lead lead zirconate titanate plates (60 mm×5 mm×0.7 mm) bonded onto a 0.3 mm thickness copper substrate. The sensor plate is 0.5 inch diameter, 0.3 mm thick copper disk soldered onto the tip of the substrate. A function generator input 10 Volt amplitude sinusoidal wave to one lead zirconate titanate plate and the output voltage from the second lead zirconate titanate plate is measured from oscilloscope at the resonant frequency determined by 90° phase shift between input and output voltage. The transducer is first calibrated in air and then output voltage is measured when the sensor disk is immersed into several testing fluids, whose viscosities are verified by rotational viscometers DV-II and DV-III from Brookfield Engineering. All the measurements are taken at 25° C.

Figure 17:
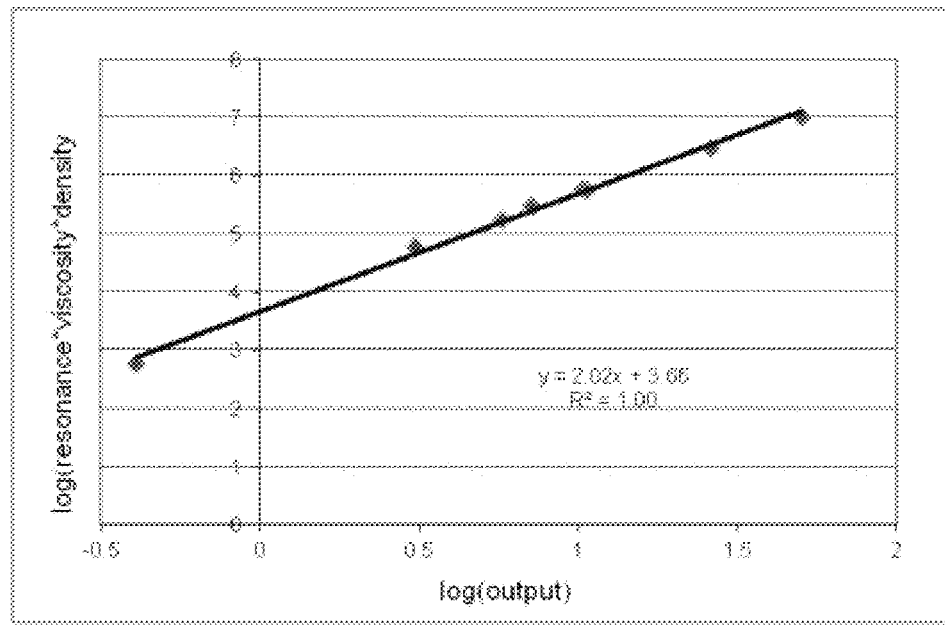
FIG. 17 illustrates the relation between frequency response and the product of the density and viscosity of the testing fluids for the electromechanical transducer employing voltage response method.

The measured resonant frequency fr and output voltage Vp of the transducer is shown in Table.1. The product of fluid density and viscosity vs output function is $$\frac{f_0 F_a(f_0)}{f_1 F_f(f_1)} - 1$$

is plotted in FIG. 17. In log-log scale, a slope of 2 predicted from Eq(7) is accurately represented by the measurement results.

TABLE 1

Measured resonant frequencies and voltage responses of the piezoelectric viscometer with 8 sample fluids.

| Samples | fr, Hz | Vp, V | density, g/cc | viscosity, cp |
|---|---|---|---|---|
| air | 628.5 | 13.2 | | |
| 100 cp | 621.7 | 3.26 | 0.965 | 96 |
| S200 | 615 | 1.98 | 0.84 | 330 |
| 500 cp | 610.7 | 1.66 | 0.965 | 492 |
| 1000 cp | 607.7 | 1.2 | 0.965 | 975 |
| 5000 cp | 600 | 0.51 | 0.965 | 5060 |
| water | 629.5 | 9.36 | 1 | 0.9 |
| carpol GP5015 | 602 | 1.18 | 1 | 920 |
| corn syrup | 536 | 0.3 | 1.33 | 14000 |

Viscosity Measurement Using Conductance Response Method

Figure 18:
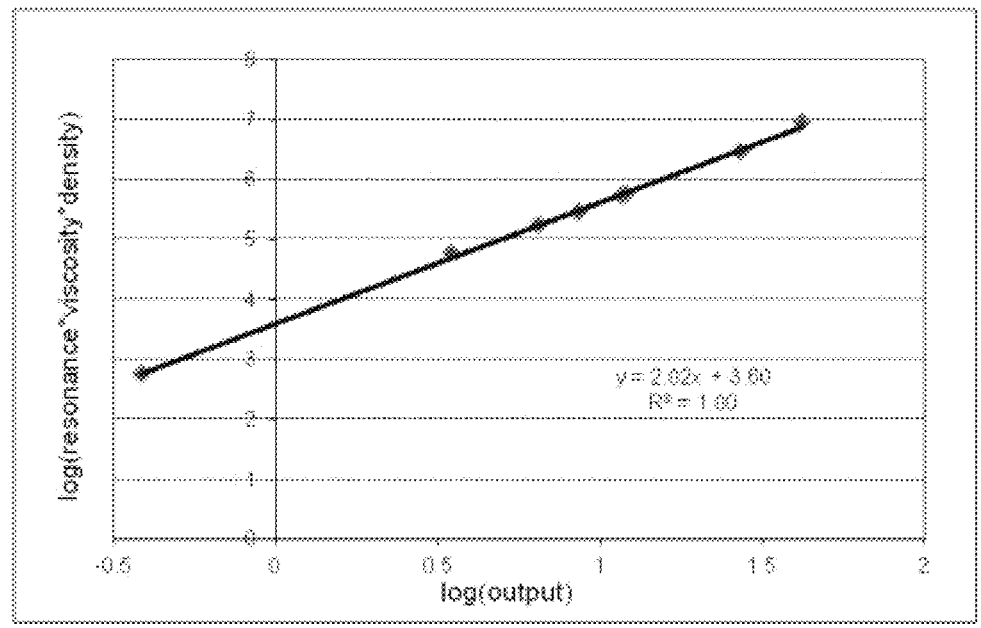
FIG. 18 illustrates the relation between electrical conductance response and the product of the density and viscosity of the testing fluid for the electromechanical transducer employing conductance response method.

The conductance of the same transducer is measured using HP 4194 impedance/Gain-Phase analyzer. The conductance of the transducer in air is first obtained at its resonant frequency. Then the conductance of the transducer is obtained at corresponding resonances when sensor disk is immersed in the same testing fluids. The resonant frequencies fr and conductance G are shown in Table.2. The product of density and viscosity of the fluids vs measured conductance function $$\frac{G_m^{air}(f_0)}{G_m^{fluid}(f_1)} - 1$$

as output is plotted in FIG. 18. In log-log scale, a slope of 2 predicted by Eq(9) is accurately represented by the measurement results.

TABLE 2

Measured resonant frequencies and conductance of the piezoelectric viscometer with 8 sample fluids.

| Samples | fr, Hz | G, uS | density, g/cc | viscosity, cp |
|---|---|---|---|---|
| air | 635.5 | 31.76 | | |
| 100 cp | 624 | 7.1 | 0.965 | 96 |
| S200 | 617 | 4.26 | 0.84 | 330 |
| 500 cp | 610 | 3.33 | 0.965 | 492 |
| 1000 cp | 601 | 2.44 | 0.965 | 975 |
| 5000 cp | 575 | 1.13 | 0.965 | 5060 |
| water | 634 | 22.9 | 1 | 0.9 |
| carpol GP5015 | 599 | 2.51 | 1 | 920 |
| corn syrup | 472 | 0.74 | 1.33 | 14000 |

The invention claim is:

1. An electromechanical transducer for measuring viscosity of a fluid, said transducer comprising:
    plural of parallel composite beams of identical length, where each composite beam is comprised of one substrate sandwiched between two electromechanical transduction materials,
    wherein said composite beams are attached to a common supporting structure at one end and are rigidly connected together at the other end with at least one sensor plate attached at this end;
    wherein the normal direction of the said sensor plate is orthogonal to the normal direction of the said composite beams; and
    a recess on the sensor plate controlling the immersion depth in the fluid.

2. An electromechanical transducer according to claim 1, wherein a drive circuit capable of frequency sweeping is used to drive the two electromechanical transduction materials as a mean to excite bending vibration of the plural composite beams with amplitude anti-node at the end of the sensor plate.

3. An electromechanical transducer according to claim 1, wherein the said plural composite beams vibrate in phase.

4. An electromechanical transducer according to claim 1, wherein the voltage generated from separate plural electromechanical transduction materials is measured as output.

5. An electromechanical transducer according to claim 1, wherein the two electromechanical transduction materials used for vibration excitation can be from one or separate composite beams.

6. An electromechanical transducer according to claim 1, wherein the two electromechanical transduction materials used for output voltage generation can be from one or separate composite beams.

7. An electromechanical transducer according to claim 1, wherein the two electromechanical transduction materials used for vibration excitation are polarized in the same direction and are electrically connected in parallel to admit the input voltage.

8. An electromechanical transducer according to claim 1, wherein the two electromechanical transduction materials used for output voltage generation are polarized in the opposite direction and are electrically connected in series.

9. An electromechanical transducer according to claim 1, when an alternating electrical input signal is used to drive the two electromechanical transduction materials as a mean to excite a bending vibration of the said plural of composite beams, an alternating electrical output signal is generated from separate the two electromechanical transduction materials having an amplitude and phase relationship to the input signal that can be used to determine the viscosity of the fluid.

10. An electromechanical transducer according to claim 1, where the two electromechanical transduction materials from said plural of parallel composite beams are polarized in the same direction and are electrically connected in parallel such that when an alternating electrical signal is applied to the two electromechanical transduction materials, said plural of parallel composite beams are excited into a bending vibration whose conductance can be used to determine the viscosity of the fluid.

11. A method of obtaining viscosity of a fluid utilizing a transducer having a composite beam made of a substrate sandwiched between two electromechanical transduction materials, a supporting structure and a sensor plate attached to opposite ends of the composite beam, wherein the normal directions of the sensor plate and the composite beam are orthogonal to each other, a recess on the sensor plate controlling the immersion depth in the fluid, comprising:
    inputting an alternative voltage to one electromechanical transduction material to set up bending vibration of the composite beam;
    outputting an alternative voltage from second electromechanical transduction material; and
    deriving viscosity of the fluid from the product of the frequency and the ratio of output to input voltages at the resonance of the vibration.

\* \* \* \* \*